US010080790B2

(12) United States Patent
Oscherwitz et al.

(10) Patent No.: US 10,080,790 B2
(45) Date of Patent: Sep. 25, 2018

(54) *STAPHYLOCOCCUS AUREUS* MATERIALS AND METHODS

(71) Applicant: THE REGENTS OF THE UNIVERSITY OF MICHIGAN, Ann Arbor, MI (US)

(72) Inventors: Jon Oscherwitz, Ann Arbor, MI (US); Kemp Cease, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/511,827

(22) PCT Filed: Sep. 17, 2015

(86) PCT No.: PCT/US2015/050678
§ 371 (c)(1),
(2) Date: Mar. 16, 2017

(87) PCT Pub. No.: WO2016/044588
PCT Pub. Date: Mar. 24, 2016

(65) Prior Publication Data
US 2017/0246284 A1 Aug. 31, 2017

Related U.S. Application Data

(60) Provisional application No. 62/052,907, filed on Sep. 19, 2014.

(51) Int. Cl.
*A61K 39/00* (2006.01)
*A61K 39/02* (2006.01)
*A61K 39/085* (2006.01)
*A61K 45/06* (2006.01)
*A61K 39/40* (2006.01)
*C07K 16/12* (2006.01)

(52) U.S. Cl.
CPC ............ *A61K 39/085* (2013.01); *A61K 39/40* (2013.01); *A61K 45/06* (2013.01); *C07K 16/1271* (2013.01); *A61K 2039/505* (2013.01); *C07K 2317/24* (2013.01); *C07K 2317/56* (2013.01); *C07K 2317/565* (2013.01); *C07K 2317/76* (2013.01)

(58) Field of Classification Search
CPC .................................................... A61K 39/085
See application file for complete search history.

(56) References Cited

U.S. PATENT DOCUMENTS

| 4,816,397 A | 3/1989 | Boss et al. |
|---|---|---|
| 4,816,567 A | 3/1989 | Cabilly et al. |
| 5,225,539 A | 7/1993 | Winter |
| 5,530,101 A | 6/1996 | Queen et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,585,089 A | 12/1996 | Queen et al. |
| 5,766,886 A | 6/1998 | Studnicka et al. |
| 5,807,715 A | 9/1998 | Morrison et al. |
| 5,874,299 A | 2/1999 | Lonberg et al. |
| 5,877,397 A | 3/1999 | Lonberg et al. |
| 6,162,963 A | 12/2000 | Kucherlapati et al. |
| 6,255,458 B1 | 7/2001 | Lonberg et al. |
| 6,300,129 B1 | 10/2001 | Lonberg et al. |
| 6,331,415 B1 | 12/2001 | Cabilly et al. |
| 6,407,213 B1 | 6/2002 | Carter et al. |
| 6,673,986 B1 | 1/2004 | Kucherlapati et al. |
| 6,713,610 B1 | 3/2004 | Kucherlapati et al. |
| 2008/0131457 A1 | 6/2008 | Taylor et al. |
| 2011/0027265 A1 | 2/2011 | Bubeck-Wardenburg et al. |
| 2013/0164308 A1 | 6/2013 | Foletti et al. |
| 2014/0079709 A1 | 3/2014 | Aman et al. |
| 2014/0154286 A1 | 6/2014 | Malley et al. |

FOREIGN PATENT DOCUMENTS

| EP | 0546073 A1 | 6/1993 |
|---|---|---|
| EP | 0239400 B1 | 8/1994 |
| EP | 0592106 B1 | 11/2004 |
| EP | 0519596 B1 | 2/2005 |
| WO | WO-1990/04036 A1 | 4/1990 |
| WO | WO-1991/09967 A1 | 7/1991 |
| WO | WO-1991/10741 A1 | 7/1991 |
| WO | WO-1993/17105 A1 | 9/1993 |
| WO | WO-1994/02602 A1 | 2/1994 |
| WO | WO-1996/33735 A1 | 10/1996 |
| WO | WO-1998/24893 A2 | 6/1998 |
| WO | WO-1999/10494 A2 | 3/1999 |

(Continued)

OTHER PUBLICATIONS

Abboud et al., Immunogenicity of *Bacillus anthracis* protective antigen domains and efficacy of elicited antibody responses depend on host genetic background. *Clin. Vaccine Immunol.* 15: 1115-23 (2008).

Adhikari et al., Novel structurally designed vaccine for *S. aureus* α-hemolysin: Protection against bacteremia and pneumonia. *PLoS One*, 7: e38567 (2012).

Al-Lazikani et al., Standard conformations for the canonical structures of immunoglobulins. *J Mol. Biol.* 273: 927-48 (1997).

Anderson et al., *Staphylococcus aureus* manganese transport protein C is a highly conserved cell surface protein that elicits protective immunity against *S. aureus* and *Staphylococcus epidermidis*. *J. Infect. Dis.* 205: 1688-96 (2012).

Arrecubieta et al., Vaccination with clumping factor A and fibronectin binding protein A to prevent *Staphylococcus aureus* infection of an aortic patch in mice. *J. Infect. Dis.* 198: 571-5 (2008).

(Continued)

*Primary Examiner* — Albert Mark Navarro

(57) ABSTRACT

The disclosure generally relates to the field of prevention and treatment of *Staphylococcus aureus* infections. In particular, the disclosure relates to immunogens comprising *Staphylococcus aureus* antigens and methods for generating immune responses to immunogens, and to antibody products specific for the *Staphylococcus aureus* epitopes and methods for treating *Staphylococcus aureus* infection with the antibody products.

10 Claims, 13 Drawing Sheets

Specification includes a Sequence Listing.

(56) References Cited

FOREIGN PATENT DOCUMENTS

WO    WO-2000/09560 A2    2/2000

OTHER PUBLICATIONS

Baca et al., Antibody humanization using monovalent phage display. *J. Biol. Chem.* 272(16): 10678-84 (1997).
Bartlett et al., α-toxin facilitates the generation of CXC chemokine gradients and stimulates neutrophil homing in *Staphylococcus aureus* pneumonia. *J. Infect. Dis.* 198: 1529-35 (2008).
Beeli et al., A tricyclic template derived from (2S,4R)-4-hydroxyproline for the synthesis of protein loop mimetics. *Helvetica Chim. Acta*, 79: 2235-48 (1996).
Berube et al., *Staphylococcus aureus* α-toxin: Nearly a centry of intrigue. *Toxins*, 5: 1140-66 (2013).
Bhakdi et al., Alpha-toxin of *Staphylococcus aureus. Microbiol. Rev.* 55: 733-51 (1991).
Bisang et al., Protein-loop mimetics: A diketopiperazine-based template to stabilize loop conformations in cyclic peptides containing the NPNA and RGD motifs. *Helvetica Chim. Acta*. 79: 1825-42 (1996).
Brady et al., Evaluation of genetically inactivated alpha toxin for protection in multiple mouse models of *Staphylococcus aureus* infection. *PLoS One*, 8: e63040 (2013).
Brady et al., Resolution of *Staphylococcus aureus* biofilm infection using vaccination and antibiotic treatment. *Infect. Immun.* 79: 1797-803 (2011).
Brossier et al., Functional analysis of *Bacillus anthracis* protective antigen by using neutralizing monoclonal antibodies. *Infect. Immun.* 72: 6313-7 (2004).
Bruggermann et al., Designer mice: the production of human antibody repertoires in transgenic animals. *Year Immunol.* 7: 33-40 (1993).
Bubeck Wardenburg et al., Surface proteins and exotoxins are required for the pathogenesis of *Staphylococcus aureus* pneumonia. *Infect. Immun.* 75: 1040-4 (2007).
Bubeck Wardenburg et al., Vaccine protection against *Staphylococcus aureus* pneumonia. *J. Exp. Med.* 205: 287-94 (2008).
Caldas et al., Design and synthesis of germline-based hemi-humanized single-chain Fv against the CD18 surface antigen. *Protein Eng.* 13(5): 353-60 (2000).
Cheung et al., Epitope-specific antibody response to the surface antigen of duck hepatitis B virus in infected ducks. *Virology*, 176: 546-52 (1990).
Cho et al., IL-17 is essential for host defense against cutaneous *Staphylococcus aureus* infection in mice. *J. Clin. Invest.* 120: 1762-1773 (2010).
Chothia et al., Canonical structures for the hypervariable regions of immunoglobulins, *J. Mol. Biol.* 196: 901-17 (1987).
Chothia et al., Conformations of immunoglobulin hypervariable regions. *Nature*, 342: 877-83 (1989).
Cole et al., Human monoclonal antibodies. *Mol. Cell. Biol.* 62: 109-20 (1984).
Coloma et al., Design and production of novel tetravalent bispecific antibodies. *Nat. Biotechnol.* 15: 159-63 (1997).
Cook et al., *Staphylococcus aureus* capsule type 8 antibodies provide inconsistent efficacy in murine models of staphylococcal infection. *Hum. Vaccin.* 5: 254-63 (2009).
Cote et al., Generation of human monoclonal antibodies reactive with cellular antigens. *Proc. Natl. Acad. Sci. USA*, 80: 2026-30 (1983).
Couto et al., Anti-BA46 monoclonal antibody Mc3: Humanization using a novel positional consensus and in vivo and in vitro characterization. *Cancer Res.* 55(8): 1717-22 (1995).
Couto et al., Designing human consensus antibodies with minimal positional templates. *Cancer Res.* 55(23 Supp): 5973s-7s (1995).
Darwish et al., Emerging therapeutic strategies to prevent infection-related microvascular endothelial activation and dysfunction. *Virulence*, 4: 572-82 (2013).

Daum et al., Progress toward a *Staphylococcus aureus* vaccine. *Clin. Infect. Dis.* 54: 560-7 (2012).
Davies et al., Antibody-antigen complexes. *Ann. Rev. Biochem.* 59: 439-73 (1990).
DeLeo et al., An antidote for *Staphylococcus aureas* pneumonia? *J. Exp. Med.* 205: 271-4 (2008).
Favre et al., Structural mimicry of canonical conformations in antibody hypervariable loops using cyclic peptides containing a heterochiral diproline template. *J. Am. Chem. Soc.* 121: 2679-85 (1999).
Foletti et al., Mechanism of action and in vivo efficacy of a human-derived antibody against *Staphylococcus aureus* α-hemolysin. *J. Mol. Biol.* 425: 1641-54 (2013).
Fredericks et al., Identification of potent human anti-IL-IR, antagonist antibodies. *Protein Engin. Des. Select.* 17: 95-106 (2004).
Gening et al., Synthetic β-(1à6)-linked N-acetylated and nonacetylated oligoglucosamines used to produce conjugate vaccines for bacterial pathogens. *Infect. Immun.* 78: 764-72 (2010).
Gillies et al., High-level expression of chimeric antibodies using adapted cDNA variable region cassettes. *J. Immunol. Methods*, 125: 191-202 (1989).
Gong et al., Evaluation of clumping factor A binding region A in a subunit vaccine against *Staphylococcus aureus*-induced mastitis in mice. *Clin. Vaccine Immunol.* 17:1746-52 (2010).
Gonzalez et al., Bacterial pore-forming toxins: the (w)hole story? *Cell. Mol. Life Sci.* 65: 493-507 (2008).
Hayden et al., Single-chain mono- and bispecific antibody derivatives with novel biological properties and antitumour activity from a COS cell transient expression system. *Ther. Immunol.* 1: 3-15 (1994).
Hering et al., Validation of the anthrax lethal toxin neutralization assay. *Biologicals*, 32: 17-27 (2004).
Holliger et al., "Diabodies": Small bivalent and bispecific antibody fragments. *Proc. Natl. Acad. Sci. USA*, 90: 6444-8 (1993).
Honegger et al., Yet another numbering scheme for immunoglobulin variable domains: an automatic modeling and analysis tool. *J. Mol. Biol.* 309(3): 657-70 (2001).
Hoogenboom et al., By-passing immunisation. Human antibodies from synthetic repertoires of germline VH gene segments rearranged in vitro. *J. Mol. Biol.* 227:381-8 (1991).
Jakobovits et al., Analysis of homozygous mutant chimeric mice: Deletion of the immunoglobulin heavy-chain joining region blocks B-cell development and antibody production. *Proc. Natl. Acad. Sci. USA*, 90: 2551-5 (1993).
Jakobovits et al., Germ-line transmission and expression of a human-derived yeast artificial chromosome. *Nature*, 362: 255-8 (1993).
Joshi et al., Immunization with *Staphylococcus aureus* iron regulated surface determinant B (lsdB) confers protection via Th17/IL17 pathway in a murine sepsis model. *Hum. Vaccin. Immunother.* 8: 336-46 (2012).
Kennedy et al., Targeting of alpha-hemolysin by active or passive immunization decreases severity of USA300 skin infection in a mouse model. *J. Infect. Dis.* 202: 1050-1058 (2010).
Kirkland et al., Analysis of the fine specificity and cross-reactivity of monoclonal anti-lipid A antibodies. *J. Immunol.* 137: 3614-9 (1986).
Kohler et al., Continuous cultures of fused cells secreting antibody of predefined specificity. *Nature*, 256: 495-7 (1985).
Kohler, Immunoglobulin chain loss in hybridoma lines. *Proc. Natl . Acad. Sci. USA*, 77(4): 2197-9 (1980).
Kozbor et al., Specific immunoglobulin production and enhanced tumorigenicity following ascites growth of human hybridomas. *J. Immunol. Methods*, 81: 31-42 (1985).
Lefranc et al., IMGT unique numbering for immunoglobulin and T cell receptor constant domains and Ig superfamily C-like domains. *Dev. Comp. Immunol.* 29: 185-203 (2005).
Li et al., Comparative analysis of virulence and toxin expression of global community-associated methicillin-resistant *Staphylococcus aureus* strains. *J. Infect. Dis.* 202: 1866-76 (2010).
Li et al., Evolution of virulence in epidemic community-associated methicillin-resistant *Staphylococcus aureus. Proc. Natl. Acad. Sci. USA*, 106: 5883-8 (2009).

(56) References Cited

OTHER PUBLICATIONS

Little et al., Characterization of lethal factor binding and cell receptor binding domains of protective antigen of *Bacillus anthracis* using monoclonal antibodies. *Microbiology*, 142: 707-15 (1996).
Little et al., Defining a serological correlate of protection in rabbits for a recombinant anthrax vaccine. *Vaccine*, 22: 422-30 (2004).
Little et al., Production and characterization of monoclonal antibodies to the protective antigen component of *Bacillus anthracis* toxin. *Infect. Immun.* 56: 1807-13 (1988).
Lonberg et al., Antigen-specific human antibodies from mice comprising four distinct genetic modifications. *Nature*, 368: 856-9 (1994).
Mallender et al., Construction, expression, and activity of a bivalent bispecific single-chain antibody. *J. Biol. Chem.* 269: 199-206 (1994).
Marks et al., By-passing immunization. Human antibodies from V-gene libraries displayed on phage. *J. Mol. Biol.* 222: 581-97 (1991).
Meijvis et al., Treatment with anti-inflammatory drugs in community-acquired pneumonia. *J. Internal Med.* 272: 25-35 (2012).
Mendez et al., Functional transplant of megabase human immunoglobulin loci recapitulates human antibody response in mice. *Nat. Genet.* 15: 146-56 (1997).
Menzies et al., Passive immunization with antiserum to a nontoxic alpha-toxin mutant from *Staphylococcus aureus* is protective in a murine model. *Infect. Immun.* 64: 1839-41 (1996).
Menzies et al., Site-directed mutagenesis of the alpha-toxin gene of *Staphylococcus aureus*: role of histidines in toxin activity in vitro and in a murine model. *Infect. Immun.* 62: 1843-7 (1994).
Migone et al., Raxibacumab for the treatment of inhalational anthrax. *N. Eng. J. Med.* 361: 135-44 (2009).
Moldenhauer et al., Identity of HML-1 antigen on intestinal intraepithelial T cells and of B-ly7 antigen on hairy cell leukaemia. *Scand. J. Immunol.* 32: 77-82 (1990).
Molne et al., Role of gamma/delta T cell receptor-expressing lymphocytes in cutaneous infection caused by *Staphylococcus aureus*. *Clin. Exp. Immunol.* 132: 209-15 (2003).
Morea et al., Antibody modeling: implications for engineering and design. *Methods*, 20(3): 267-79 (2000).
Morel et al., Monoclonal antibodies to bovine serum albumin: affinity and specificity determinations. *Mol. Immunol.* 25: 7-15 (1988).
Moreno et al., Cytotoxic CD4+ T cells from a sporozoite-immunized volunteer recognize the Plasmodium falciparum CS protein. *Int. Immunol.* 3: 997-1003 (1991).
Morrison, Transfectomas provide novel chimeric antibodies., *Science*, 229: 1202 (1985).
Munoz-Planillo et al., A critical role for hemolysins and bacterial lipoproteins in *Staphylococcus aureus*-induced activation of the Nlrp3 inflammasome. *J. Immunol.* 183: 3942-8 (2009).
Nicholls et al., An improved method for generating single-chain antibodies from hybridomas. *J. Immunol. Meth.* 165: 81-91 (1993).
Nilsson et al., Alpha-toxin and gamma-toxin jointly promote *Staphylococcus aureus* virulence in murine septic arthritis. *Infect. Immun.* 67: 1045-9 (1999).
Nygaard et al., Alpha-toxin induces programmed cell death of human T cells, B cells, and monocytes during USA300 infection. *PLoS One*, 7: e36532 (2012).
Oi et al., Chimeric antibodies. *BioTechniques*, 4(3): 214-21 (1986).
Oscherwitz et al., A heterologous helper T-cell epitope enhances the immunogenicity of a multiple-antigenic-peptide vaccine targeting the cryptic loop-neutralizing determinant of *Bacillus anthracis* protective antigen. *Infect. Immun.* 77: 5509-18 (2009).
Oscherwitz et al., A synthetic peptide vaccine directed against the 2β2-2β3 loop of domain 2 of protective antigen protects rabbits from inhalation anthrax. *J. Immunol.* 185: 3661-8 (2010).
Oscherwitz et al., In vivo mapping of a protective linear neutralizing epitope at the N-terminus of alpha hemolysin from *Staphylococcus aureus*. *Mol. Immunol.* 60: 62-71 (2014).
Oscherwitz et al., Recombinant vaccine displaying the loop-neutralizing determinant from protective antigen completely protects rabbits from experimental inhalation anthrax. *Clin. Vaccine Immunol.* 20:341-9 (2013).
Oscherwitz et al., Synthetic peptide vaccine targeting a cryptic neutralizing epitope in domain 2 of *Bacillus anthracis* protective antigen. *Infect. Immun.* 77: 3380-8 (2009).
Otto, Basis of virulence in community-associated methicillin-resistant *Staphylococcus aureus*. *Annu. Rev. Microbiol.* 64: 143-62 (2010).
Padlan, A possible procedure for reducing the immunogenicity of antibody variable domains while preserving their ligand-binding properties. *Mol. Immunol.* 28(4/5): 489-98 (1991).
Panina-Bordignon et al., Universally immunogenic T cell epitopes: promiscuous binding to human MHC class II and promiscuous recognition by T cells. *Eur. J. Immunol.* 19: 2237-42 (1989).
Pedersen et al., Comparison of surface accessible residues in human and murine immunoglobulin Fv domains. Implication for humanization of murine antibodies. *J. Mol. Biol.* 235(3): 959-73 (1994).
Pfeifer et al., Stabilisation of β-hairpin conformations in a protein surface mimetic using a bicyclic template derived from (2S,3R,4R)-diaminoproline. *Chem. Commun.* 18: 1977-8 (1998).
Plaut et al., Stably luminescent *Staphylococcus aureus* clinical strains for use in bioluminescent imaging. *PLoS One*, 8: e59232 (2013).
Poljak et al., Production and structure of diabodies. *Structure*, 2: 1121-3 (1994).
Powers et al., Expression of single-chain Fv-Fc fusions in Pichia pastoris. *J. Immunol. Meth.* 251: 123-35 (2001).
Prabhakara et al., Epicutaneous model of community-acquired *Staphylococcus aureus* skin infections. *Infect. Immun.* 81: 1306-15 (2013).
Proudfoot, Transcriptional interference and termination between duplicated alpha-globin gene constructs suggests a novel mechanism for gene regulation. *Nature*, 322(6079): 562-5 (1986).
Raghavendran et al., Pharmacotherapy of acute lung injury and acute respiratory distress syndrome. *Curr. Med. Chem.* 15: 1911-24 (2008).
Ragle et al., Anti-alpha-hemolysin monoclonal antibodies mediate protection against *Staphylococcus aureus* pneumonia. *Infect. Immun.* 77: 2712-8 (2009).
Rauch et al., Abscess formation and alpha-hemolysin induced toxicity in a mouse model of *Staphylococcus aureus* peritoneal infection. *Infect. Immun.* 80: 3721-32 (2012).
Reason et al., Frequency and domain specificity of toxin-neutralizing paratopes in the human antibody response to anthrax vaccine adsorbed. *Infect. Immun.* 77: 2030-5 (2009).
Riechmann et al., Reshaping human antibodies for therapy. *Nature*, 332(6162): 323-7 (1988).
Roguska et al., A comparison of two murine monoclonal antibodies humanized by CDR-grafting and variable domain resurfacing. *Protein Eng.* 9(10): 895-904 (1996).
Roguska et al., Humanization of murine monoclonal antibodies through variable domain resurfacing. *Proc. Natl. Acad. Sci. USA*, 91: 969-73 (1994).
Sandhu, A rapid procedure for the humanization of monoclonal antibodies. *Gene*, 150(2): 409-10 (1994).
Shu et al., Secretion of a single-gene-encoded immunoglobulin from myeloma cells. *Proc. Natl. Acad. Sci. USA*, 90: 7995-9 (1993).
Snippe et al., Adjuvant effect of nonionic block polymer surfactants in humoral and cellular immunity. *Int. Arch. Allergy Appl. Immunol.* 65: 390-8 (1981).
Song et al., Structure of staphylococcal alpha-homolysin, a heptameric transmembrane pore. *Science*, 274: 1859-66 (1996).
Stahli et al., Distinction of epitopes by monoclonal antibodies. *Meth. Enzymol.* 92: 242-53 (1983).
Studnicka et al., Human-engineered monoclonal antibodies retain full specific binding activity by preserving non-CDR complementarity-modulating residues. *Protein Eng.* 7(6): 805-14 (1994).
Tan et al., "Superhumanized" antibodies: reduction of immunogenic potential by complementarity-determining region grafting with human germline sequences: Application to an anti-CD28. *J. Immunol.* 169: 1119-25 (2002).

(56) References Cited

OTHER PUBLICATIONS

Thirion et al., Mono- and bispecific single-chain antibody fragments for cancer therapy. *Eur. J. Cancer Prev.* 5: 507-11 (1996).

Tkaczyk et al., Identification of anti-alpha toxin monoclonal antibodies that reduce the severity of *Staphylococcus aureus* dermonecrosis and exhibit a correlation between affinity and potency. *Clin. Vaccine Immunol.* 19(3): 377-85 (2012).

Tkaczyk et al., *Staphylococcus aureus* alpha toxin suppresses effective innate and adaptive immune responses in a murine dermonecrosis model. *PLoS One*, 8: e75103 (2013).

Tominaga et al., Japanese standard reference material JDS Lot 2 for haemoglobin A1c. II: Present state of standardization of haemoglobin A1c in Japan using the new reference material in routine clinical assays. *Anal. Commun.* 36: 47-50 (1999).

Verhaar et al., A single chain Fv derived from a filamentous phage library has distinct tumor targeting advantages over one derived from a hybridoma. *Int. J. Cancer*, 61: 497-501 (1995).

Wang et al., Identification of novel cytolytic peptides as key virulence determinants for community-associated MRSA. *Nat. Med.* 13: 1510-4 (2007).

Wilke et al., Role of a disintegrin and metalloprotease 10 in *Staphylococcus aureus* alpha-hemolysin-mediated cellular injury. *Proc. Natl. Acad. Sci. USA*, 107: 13473-8 (2010).

FIGURE 5

| | | Alpha Toxin Sequence | Antibody EC$_{50}$ | TNA ED$_{50}$ |
|---|---|---|---|---|
| | | 114                                       147 STLTYGFNGNVTGDDTGKIGGLIGANVSIGHTLK | | |
| MAP | 114-131 | STLTYGFNGNVTGDDTGK | | |
| | 119-139 | GFNGNVTGDDTGKIGGLIGAN | | * |
| | 122-137 | GNVTGDDTGKIGGLIG | | |
| | 130-147 | GKIGGLIGANVSIGHTLK | | |

STAPHYLOCOCCUS AUREUS MATERIALS AND METHODS

This application claims priority to the Sep. 19, 2014 filing date of U.S. Provisional Application No. 62/052,907, which is incorporated by reference herein in its entirety.

STATEMENT OF GOVERNMENT INTEREST

This invention was made with Government support under I01BX000429-01A2 awarded by the United States Department of Veterans Affairs. The Government has certain rights in the invention.

INCORPORATION BY REFERENCE OF THE SEQUENCE LISTING

This application contains, as a separate part of disclosure, a Sequence Listing in computer-readable form (filename: 48424PCT_SeqListing.txt; 4,910 bytes—ASCII text file; created Sep. 17, 2015) which is incorporated by reference herein in its entirety.

FIELD

The disclosure generally relates to the field of prevention and treatment of *Staphylococcus aureus* infections. In particular, the disclosure relates to immunogens comprising *Staphylococcus aureus* epitopes and methods for generating immune responses to the epitopes, and to antibody products specific for the *Staphylococcus aureus* epitopes and methods for treating *Staphylococcus aureus* infection with the antibody products.

BACKGROUND

*Staphylococcus aureus* (*S. aureus*) is a gram positive bacteria that is a common pathogen in hospitals. Infection with *S. aureus* often results in severe and destructive infections of the skin and soft tissues. Uncontrolled infection, especially in vulnerable patients, may spread to many tissues and organs, notably including joints, heart valves, and the lungs, often leading to sepsis and death. A significant proportion of these infections are the result of methicillin-resistant *S. aureus* (MRSA), and many strains are in fact resistant to multiple antibiotics. Contagious and antibiotic-resistant *S. aureus* strains are termed Methicillin-resistant *Staphylococcus aureus* (MRSA). One such strain, community-associated MRSA (CA-MRSA), has emerged as a notoriously virulent and lethal cause of pneumonia even in the young and healthy. In general, there has been a dramatic increase in the proportion of cases attributable to MRSA which is now the cause of 50% of all *S. aureus* infections in some intensive care units. By some estimates, 20-40% of all hospital-acquired pneumonia in the US, including ventilator-associated pneumonia (VAP), is due to MRSA, and VAP due to MRSA is associated with a poorer outcome compared to VAP with other pathogens.

In primary bacterial pneumonia, including *S. aureus* pneumonia, the central therapeutic focus is on killing or otherwise controlling the offending pathogen. Such interventions may take days or even weeks to be fully effective, and consequently are not optimal for rapidly countering the effects of potent and destructive virulence factors that frequently mediate pathogen-associated lung and soft tissue injury. Broad, non-specific interventions targeting the patient immune response, such as use of corticosteroids [Meijvis et al., *J. Internal Med.*, 272: 25-35 (2012)], have been used in various pulmonary infection scenarios including pneumonia, and new approaches are being explored [Raghavendran et al., *Curr. Med. Chem.*, 15: 1911-1924 (2008) and Darwish and Liles, *Virulence*, 4: 572-582 (2013)], but no general strategy for countering pathogen-associated injury has emerged.

*S. aureus* produces dozens of molecules known or thought to contribute to virulence. These include surface-expressed determinants such as Protein A, IsdB, clumping factor A (ClfA) and capsular polysacharrides, secreted exotoxins (including alpha, beta and gamma hemolysins), the phenol soluble modulins (PSMs), as well as other virulence factors [Otto, *Annual Review of Microbiology*, 64: 143-162 (2010); Wang et al., *Nat. Med.*, 13: 1510-1514 (2007); Daum and Spellberg, *Clin. Infect. Dis.*, 54: 560-567 (2012)]. Yet, despite the presence of so many well-characterized virulence factors, and efforts to evaluate many of these as vaccine targets [Gong et al., *Clinical and Vaccine Immunology*, 17:1746-1752 (2010); Arrecubieta et al., *The Journal of Infectious Diseases*, 198: 571-575 (2008); Anderson et al., *The Journal of Infectious Diseases*, 205: 1688-1696 (2012); Brady et al., *Infection and Immunity*, 79: 1797-1803 (2011); Joshi et al., *Human Vaccines & Immunotherapeutics*, 8: 336-346 (2012); Gening et al., *Infection and Immunity*, 78: 764-772 (2010); Cook et al., *Human Vaccines*, 5: 254-263 (2009)], development of an effective *S. aureus* vaccine has been elusive.

Alpha hemolysin or alpha toxin (Hla or AT; UniProtKB/Swiss-Prot P09616) is a protein ubiquitously secreted by most strains of *S. aureus* that is a critical virulence factor in *S. aureus* infection, host interaction, and pathology [DeLeo and Otto, *J. Exp. Med.*, 205: 271-274 (2008); Tkaczyk et al., *PLoS One*, 8: e75103 (2013); Berube and Wardenburg, *Toxins*, 5: 1140-1166 (2013); Cho et al., *J. Clin. Invest.* 120: 1762-1773 (2010)] (16-19). Wild-type, methicillin-sensitive *S. aureus* (MSSA) and MRSA strains associated with human disease are highly virulent in mouse pneumonia, sepsis and dermonecrosis models, yet the respective hla deletion mutants are almost completely devoid of pathogenicity [Kennedy et al., *J. Infect. Dis.*, 202: 1050-1058 (2010); Bubeck et al., *Infect. Immun.*, 75: 1040-1044 (2007)]. Importantly, the high levels of virulence associated with CA-MRSA strains, in particular pulse field gel electrophoresis type (pulsotype) USA300, which is responsible for the preponderance of skin and soft tissue infections in otherwise healthy individuals in the community, appear to be related, in part, to the high levels of AT produced by these strains [Otto, *Annual Review of Microbiology*, 64: 143-162 (2010); Li et al., *J. Infect. Dis.*, 202: 1866-1876 (2010); Li et al., *Proc. Natl. Acad. Sci. USA*, 106: 5883-5888 (2009)].

AT is a 293 residue protein that binds ADAM10 at the cell surface and then self-associates to form a heptameric structure that creates a pore in eukaryotic membranes [Bhakdi and Tranum-Jensen, *Microbiol. Rev.*, 55: 733-751 (1991); Wilke and Bubeck Wardenburg, *Proc. Natl. Acad. Sci. USA*, 107: 13473-13478 (2010)]. The heptamer pore channel is a 14-stranded beta barrel formed by contributions of a beta-hairpin loop from each of the monomeric alpha-toxin molecules [Song et al., *Science*, 274: 1859-1866 (1996)]. AT is a prototypical example of a multimeric pore-forming toxin.

Studies in the early 1990s first demonstrated that passive immunization with rabbit antibody elicited to H35L, a non-toxic mutant of AT [Menzies and Kernodle, *Infect. Immun.*, 62: 1843-1847 (1994)], is capable of mediating protection of mice from lethal *S. aureus* challenges in a model of lethal sepsis, and more recently, active immunization of mice with H35L has been shown to confer significant protection in the mouse models of pneumonia, sepsis and dermonecrosis [Kennedy, supra; Brady et al., *PLoS One*, 8: e63040 (2013); Prabhakara et al., *Infect. Immun.*, 81: 1306-1315 (2013); Menzies and Kernodle, *Infect. Immun.*, 64: 1839-1841 (1996); Rauch et al., *Infect. Immun.*, 80: 3721-3732 (2012); Bubeck Wardenburg and Schneewind, *J. Exp. Med.*, 205: 287-294 (2008)]. Passive immunization with anti-AT antibodies in a mouse model was also studied in Tkaczyk et al., *Clin. Vaccine Immunol.*, 19(3): 377-385 (2012). An immunogen comprised of the n-terminal 62 amino acids from AT with a C-terminal His-tag was capable of eliciting neutralizing Ab and protecting mice from *S. aureus* challenges in pneumonia and bacteremia models [Adhikari et al., *PLoS One*, 7: e38567 (2012)]. U.S. Patent Publication No. 2008/0131457 filed Feb. 27, 2007 also relates to vaccines comprising an *S. aureus* AT antigen. Studies in other model systems where pathology is mediated by toxin elaboration, have demonstrated that the preponderance of antibody elicited through immunization with the full length toxins are mostly non-neutralizing and nonfunctional [Abboud and Casadevall, *Clin. Vaccine Immunol.*, 15: 1115-1123 (2008); Brossier et al., *Infect. Immun.*, 72: 6313-6317 (2004); Little et al., *Infect. Immun.*, 56: 1807-1813 (1988); Little et al., *Microbiology*, 142: 707-715 (1996); Reason et al., *Infect. Immun.*, 77: 2030-2035 (2009)].

Though immunization of mice and rabbits with H35L, or other full length forms of AT, reproducibly elicit neutralizing Ab, few neutralizing epitopes in AT have been described to date. Monoclonal antibodies that neutralize AT have been reported to bind conformational epitopes in the cap region of AT in one case, and to bind sequences yet to be fully elucidated in a second case. See, respectively, Foletti et al., *J. Mol. Biol.*, 425: 1641-1654 (2013) and Tkaczyk (2012), supra. In a third example, a monoclonal antibody elicited to H35L protected mice in a pneumonia model, and bound a glutathione S-transferase fusion protein comprised of amino acids 1-50 from AT. The neutralizing epitope bound by the mAb was inferred to be conformational in nature, since it was incapable of binding the denatured 1-50 on western blot, and could not be defined by a panel of overlapping 15-mer peptides spanning the region [Ragle and Bubeck Wardenburg, *Infect. Immun.*, 77: 2712-2718 (2009)].

A need in the art therefore remains for products and methods for preventing and treating *S. aureus* infections, especially antibiotic-resistant infections.

SUMMARY

Provided herein are methods and products for preventing *S. aureus* infection and for therapeutically treating *S. aureus* infection.

In one aspect, immunogenic compositions comprising an immunogen consisting essentially of the *S. aureus* alpha toxin epitope GFNGNVTGDDTGKIGGLIGAN (SEQ ID NO: 1), or a functional equivalent thereof, are provided. The *S. aureus* alpha toxin epitope of SEQ ID NO: 1 corresponds to amino acids 119-139 of the mature form of AT and is referred to as the pore neutralizing determinant (PND) herein. In some embodiments, the immunogenic composition comprises a immunogen consisting of the PND of SEQ ID NO: 1. In some embodiments, the immunogenic compositions further comprise an adjuvant. In some embodiments, the immunogenic compositions further comprise one or more additional *S. aureus* immunogens.

In another aspect, methods of administering an immunogenic compositions disclosed herein to a subject to induce protective immunity against *S. aureus* infection are provided.

In yet another aspect, antibody products specific for the *S. aureus* alpha toxin epitope of SEQ ID NO: 1 are provided.

In some embodiments, the antibody products comprise the heavy chain complementarity determining regions (CDRs) (determined from the primary sequence in accordance with Kabat-Chotia [Al-Lazikani et al., *J Mol Biol*, 273: 927-948 (1997)], identified, for example, using the Sequence Search feature identification of the Database of Immunoglobulins with Integrated Tools [http://circe.med.uniroma1.it/digit/]).

```
CDRH1     TFSRTTYGVH,            (SEQ ID NO: 2)

CDRH2     AMWKDGTTDYNAAFMS,      (SEQ ID NO: 3)
and

CDRH3     RHYTVDF,               (SEQ ID NO: 4)

and the light chain CDRs
CDRL1     RSSQTIVHRNGNIYLE,      (SEQ ID NO: 5)

CDRL2     KVSSRFS,               (SEQ ID NO: 6)
and

CDRL3     FQGSRIPFT.             (SEQ ID NO: 7)
```

In some embodiments, the antibody products comprise the heavy chain variable region

```
                                               (SEQ ID NO: 8)
LEQSGPVLVQPLQSLAITCSVSTFSRTTYGVHWIRQSPGKGLEWLGAMWK

DGTTDYNAAFMSRLSITQDNSKSQVFLEINDLQSDDTGTYFCFDRHYTVD

FWGQGTSVTVS and the light chain variable region
                                               (SEQ ID NO: 9)
VLTQTPLSLSVSLGDQASISCRSSQTIVHRNGNIYLEWYLQKPDQSPKLL

IYKVSSRFSGVPDRFSGSGSGTDFTLRISRVEAEDLGIYYCFQGSRIPFT

FGGGTKLEIK.
```

In still another aspect, methods are provided of administering an antibody product specific for the *S. aureus* alpha toxin epitope of SEQ ID NO: 1 to a subject to treat an *S. aureus* infection. In some embodiments, the methods further comprise administering an antibody product specific for an *S. aureus* epitope different from the epitope of SEQ ID NO: 1, such as an antibody product specific for a different AT epitope or an epitope of an *S. aureus* virulence factor other than AT. In some embodiments, methods are provided of treating *S. aureus* infection in a subject comprising administering a polynucleotide encoding an antibody product specific for the *S. aureus* alpha toxin epitope of SEQ ID NO: 1.

In some embodiments, the methods disclosed herein further comprise administering one or more antibiotics. In some embodiments, the antibiotic is tetracycline, doxycycline, minocycline, trimethoprim-sulfamethoxazole, rifampin, clindamycin, vancomycin, linezolid, daptomycin, tigecycline, telavancin, dalbavancin, and oritavancin, ceftobiprole, mupirocin and/or iclaprim. In some embodiments, the methods further comprise one or more anti-infective and/or one or more anti-microbial agents.

DESCRIPTION OF THE DRAWINGS

FIG. 5 shows that antibody and TNA responses in the sera of rabbits immunized with MAP constructs displaying overlapping residues from AT. Groups of rabbits were immunized 4 times at two-week intervals with a mixture of two MAPs each containing the respective B cell target sequence (A) linked separately to the T* and P30 helper T cell epitopes. Ten days after the final immunization, rabbits were bled and sera were evaluated by ELISA for reactivity with immobilized full length AT (B) or the in the TNA (C). Bar graphs represent arithmetic means. Error bars represent SEMs. *p=0.022, one-way ANOVA; p<0.05, 119-139 vs all other groups, Newman Keuls multiple comparison test.

DESCRIPTION

Figure 1:
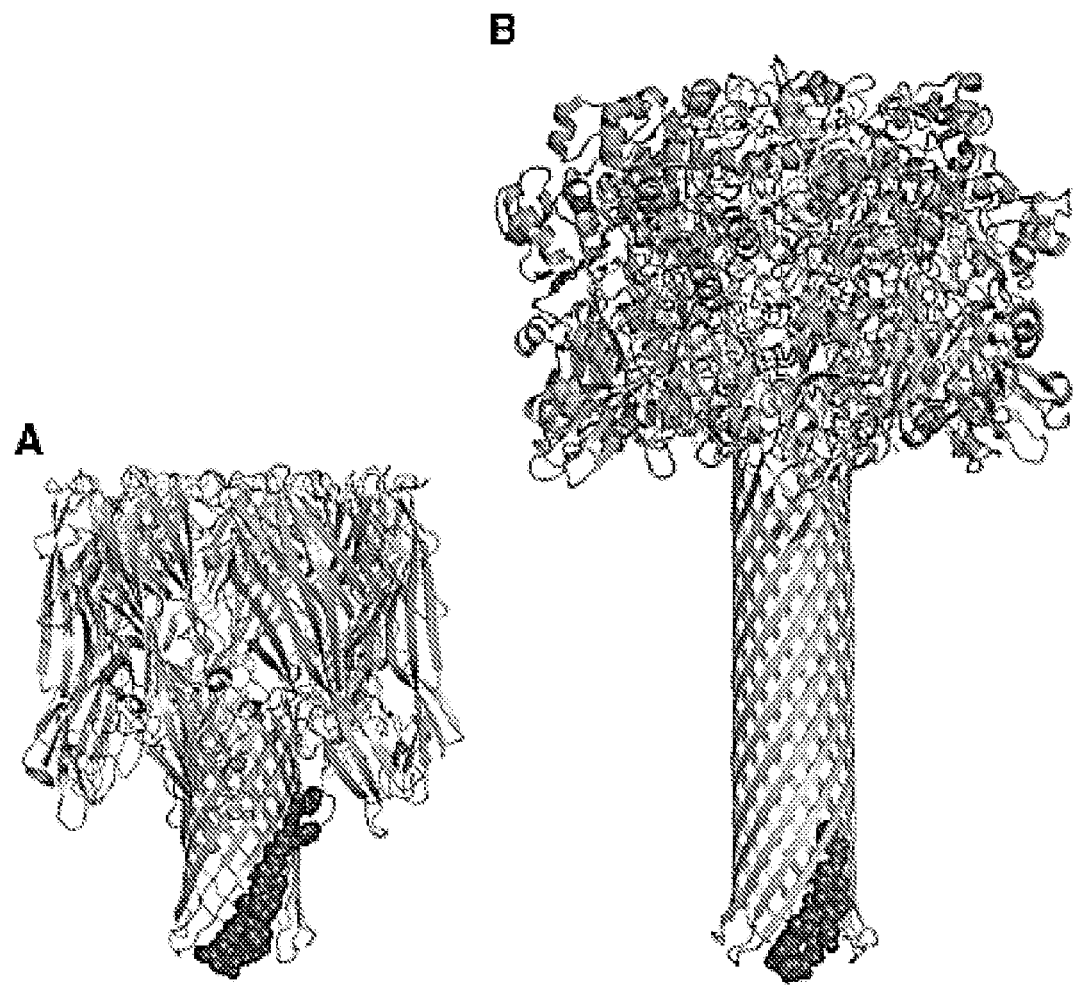
FIG. 1 shows that *S. aureus* alpha toxin (AT) and *B. anthracis* protective antigen (PA) share structural and functional homology but only limited sequence identity. Comparison of protein structural models of the heptameric AT (PDB7AHL) (A) and PA (PDB1V36) (B). Sequences in red represent aligned sequence shown in (C). Amino acid alignment of PA and AT in the region of the LND of PA demonstrates 37% sequence identity. Asterisks denote positions of amino acid identity, while periods and colons denote semi-conservative and conservative substitutions, respectively.

The following paragraphs set out more detail regarding products and methods provided herein.

As used herein, the singular forms "a", "an" and "the" are intended to include the plural forms as well, unless the context clearly indicates otherwise. Furthermore, to the extent that the terms "including", "includes", "having", "has" or "with" are used herein, such terms are intended to be inclusive in a manner similar to the term "comprising."

PND Immunogens and Compositions

An immunogen "consisting essentially" of the amino acids of SEQ ID NO: 1 (i.e., AT PND amino acids 119-139) herein means that the immunogen includes the amino acids of SEQ ID NO: 1 but may also include additional amino acids at either its N-terminus or C-terminus as long as the amino acids of the peptide originating from SEQ ID NO: 1 determine the immunogenic specificity of the peptide. For example, the PND may be part of a fusion protein immunogen as long as the PND is the part of the fusion protein immunogen that determines the immunogenic specificity of the fusion protein immunogen and the amino acids fused to it do not contribute to immunogenic specificity of the fusion protein immunogen.

In some embodiments, the PND or PND fusion protein is produced by recombinant methods. In some embodiments, the PND amino acids of SEQ ID NO: 1 are encoded by the polnucleotide sequence GGATTCAACGGTAATGT-TACTGGTGATGATACAGGAAAAATTGGCGGCCTT-ATTGGT GCAAAT (SEQ ID NO: 10). Also contemplated are all other polynucleotide sequences encoding the PND amino acids of SEQ ID NO: 1 in view of the degeneracy of the genetic code.

An "immunogenic equivalent" of the PND amino acids of SEQ ID NO: 1 herein means that the PND amino acids of SEQ ID NO: 1 in the immunogen may be deleted, substituted or chemically modified as long as the immunogen retains its immunogenic effect and specificity. Immunogenic effect herein refers to the ability of the immunogen, when introduced in to a host animal in a manner known to one skilled in the art, to elicit antibodies in the host serum to a concentration such that antibody binding to AT can be detected by a method known to one skilled in the art, such as an enzyme-linked immunosorbant assay (ELISA), and with such binding remaining demonstrable in a dilution of said serum by a factor of 16 or greater. Specificity herein refers to the ability of antibody binding to AT to be reduced by 90% or greater by a peptide PND SEQ ID NO: 1 present at a concentration of 10 micromolar or less.

In some embodiments, such immunogenic equivalents comprise an amino acid sequence which is at least 60%, 70%, 80%, 90%, 95% or 98% identical to SEQ ID NO: 1. Sequence comparisons can be conducted by eye, or more usually, with the aid of readily available sequence comparison programs standard in the art.

In some embodiments, amino acid substitutions are conservative amino acid substitutions. Conservative substitution tables providing functionally similar amino acids are well known in the art. Conservative substitutions may be made, for example according to the Table 1 below. Amino acids in the same block in the second column and preferably in the same line in the third column may be substituted for each other.

TABLE 1

CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, .beta.-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Penylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

In some embodiments, an immunogenic equivalent of SEQ ID NO: 1 is a "mimetic" or "peptidomimetic," that is a synthetic chemical compound that has substantially the same immunogenic characteristics of the SEQ ID NO: 1. The mimetic can be either entirely composed of synthetic, non-natural analogues of amino acids, or, is a chimeric molecule of partly natural peptidyl amino acids and partly non-natural analogs of amino acids. Mimetics can also incorporate any amount of natural amino acid conservative substitutions as long as such substitutions also do not substantially alter the mimetics' structure and/or activity. As with polypeptides of the present disclosure which are conservative variants, routine experimentation will determine whether a mimetic is within the scope of the disclosure, i.e., that its structure and/or function is not substantially altered.

Non-natural structural components contemplated herein are typically from three structural groups: a) residue linkage groups other than the natural amide bond ("peptide bond") linkages; b) non-natural residues in place of naturally occurring amino acid residues; or c) residues which induce secondary structural mimicry (i.e., to induce or stabilize a secondary structure such as a beta turn, gamma turn, beta sheet or alpha helix conformation). Residue linkage groups can be peptide bonds, other chemical bonds or other coupling means including, but not limited to, glutaraldehyde, N-hydroxysuccinimide esters; bifunctional maleimides; $N_5N'$-dicyclohexylcarbodiimide (DCC) or N,N'-diisopropylcarbodiimide (DIC). Linking groups that can be an alternative to the traditional amide bond ("peptide bond") linkages include, but are not limited to, ketomethylene (e.g., —C(=O)—CH$_2$— for ~C(=O)~NH~), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester. See, e.g., Spatola, pp. 267-357 in Chemistry and Biochemistry of Amino Acids, Peptides and Proteins, Vol. 7, "Peptide Backbone Modifications," Marcell Dekker, N.Y (1983).

In some embodiments, immunogenic equivalents may be modified to be more resistant to hydrolysis by proteases, such as by containing D-amino acids or one or more non-hydrolyzable peptide bonds linking amino acids. Non-hydrolyzable peptide bonds are well-known in the art and may include -psi[CH$_2$NH]-reduced amide peptide bonds, -psi[COCH$_2$]-ketomethylene peptide bonds, -psi[CH(CN) NH]-(cyanomethylene)amino peptide bonds, -psi[CH$_2$CH (OH)]-hydroxyethylene peptide bonds, -psi[CH$_2$O] peptide bonds, and -psi[CH$_2$S]-thiomethylene peptide bonds. In some embodiments, immunogenic equivalents may comprise unnatural and unusual amino acids and amino acid analogs, such as ornithine, norleucine, L-malonyltyrosine and others known to those of skill in the art. Other examples include D-isomer amino acids, N-methyl amino acids, L-isomer amino acids, modified L-isomer amino acids and cyclized derivatives.

In some embodiments, the immunogens comprise amino acid residues located at or near the N-terminus and/or C-terminus that have side chains suitable for the formation of an intramolecular crosslink for purposes of cyclizing the peptides. Suitable residues for crosslinking are well known to a person of skill in the art and may comprise disulfide (cysteine-cysteine), thioether (cysteine-electrophile, such as bromoacetyl, maleimidyl etc.) and other bonds. In some embodiments, the crosslink for cyclization is provided by a disulfide bridge between cysteine residues located at or near the N and/or C termini of the peptides. In some embodiments, terminal spacer residues are added to the peptides of the disclosure in order to ensure the spatial accessibility of the crosslinking residues, such as for the incorporation of the cyclic peptide into liposomes, virosomes, or other suitable delivery vehicles. For example, a GGC sequence may be added to the N-terminus and an additional glycine residue at the C-terminus, but many other spacer sequences known to those of skill in the art may be used for the purposes of the present disclosure, as long as the side chains of the spacer residues are small enough so as not to sterically interfere with the intramolecular crosslink. Examples of suitable spacer residues comprise amino acids such as alanine, serine, asparagine, glutamine, or glycine. In some embodiments, the peptides of the present disclosure and immunogenic equivalents thereof are cyclized by the use of a template. One advantage of using such widely available templates is their rigidity that may stabilize the three-dimensional conformation of the cyclized peptides more effectively than the use of internal crosslinks which typically introduce several rotatable bonds, thereby destabilizing the cyclized peptide structure. Suitable templates for the cyclization of peptide chains are well known in the art and may be tricyclic (Beeli et al., Helvetica Chimica Acta 79: 2235 2248, 1996), diketopiperazine-based (Bisang et al., Helvetica Chimica Acta 79: 1825 1842, 1996), bicyclic, such as a template derived from differentially substituted diaminoprolines (Pfeifer et al., Chem. Commun. 1977 78, 1998) or heterochiral diprolines (Favre et al. J. Am. Chem. Soc. 121: 2679 2685, 1999), to name only a few. Thus, in some embodiments, immunogens are cyclized by the formation of an intramolecular crosslink.

In some embodiments, the immunogens are synthesized in linear form and purified prior to conjugation to a branching or dendrimeric core structure. In some embodiments, the immunogens are configured in a branching manner by synthesis from, or conjugation to, a suitable core or backbone structure. In some embodiments, the immunogens are synthesized from four or eight initiation sites comprised of the a- and ε-amines of a branching lysine core so as to result in what has been termed a multiple antigen structure.

In some embodiments, the PND amino acids are repeated in the immunogen.

In some embodiments, the immunogen can be a fusion protein of the PND amino acids with *Escherichia coli* maltose binding protein or derivatives thereof.

The immunogens disclosed herein can be produced and purified by standard methods in the art.

The terms "purified" or "to purify" refer to the removal of contaminants or undesired compounds from a sample or composition. As used herein, the term "substantially purified" refers to the removal of from about 70 to 90%, up to 100%, of the contaminants or undesired compounds from a sample or composition.

In some embodiments, immunogens can be loaded, by encapsulation or surface attachment, onto virosomes, liposomes, or nanoparticles.

Compositions of immunogens (i.e., immunogenic compositions) are provided herein. As used herein, the term "immunogen" refers to a peptide or that is capable of eliciting an immune response in a subject. The immunogenic compositions are formulated as dosage forms appropriate for the desired route of administration. For example, the immunogenic compositions can be solutions, suspension, emulsions, syrups, tablets, capsules (each including timed release and sustained release formulations), pills, powders, granules, elixirs or tinctures. Methods for preparing various dosage forms are known or apparent to those skilled in the art and are described in more detail in, for example, Remington: The Science and Practice of Pharmacy ("Remington's Pharmaceutical Sciences") Gennaro A R Ed. 20th edition, 2000: Williams & Wilkins Pa., USA.

In some embodiments, the immunogenic compositions comprise the immunogen, or a immunogenic equivalent thereof, dissolved or suspended in an pharmaceutically acceptable carrier (i.e., excipient), preferably an aqueous carrier. As used herein, the terms "pharmaceutically acceptable" or "pharmacologically acceptable" refer to ingredients or compositions that do not substantially produce adverse reactions (e.g., toxic, allergic, or immunological reactions) when administered to a subject. A variety of aqueous carriers may be used including, but not limited to, water, buffered water, 0.4% saline, 0.3% glycine, hyaluronic acid, and the like. Yet other examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants. The resulting aqueous pharmaceutical compositions may be packaged for use as is, or lyophilized, the lyophilized preparation being combined with a sterile solution prior to administration.

In some embodiments, the immunogenic compositions contemplated also comprise an adjuvant. An "adjuvant" as used herein refers to an antigen-nonspecific stimulator of the immune response. Most adjuvants incorporate two components. One component is designed to protect the antigen from rapid catabolism (e.g., liposomes or synthetic surfactants [Snippe et al., *Int Arch Allergy Appl Immunol.*, 65: 390-398 (1981)]. The other component is a substance that will stimulate the immune response nonspecifically. These substances act by raising the level of lymphokines Lymphokines stimulate the activity of antigen-processing cells directly and cause a local inflammatory reaction at the site of injection. Adjuvants contemplated herein include, but are not limited to, Freund's adjuvant, mineral gels (e.g., aluminum hydroxide and aluminum phosphate), and surface active substances (e.g., lysolecithin, pluronic polyols, polyanions, keyhole limpet hemocyanin, and dinitrophenol). Other adjuvants contemplated include, but are not limited to BCG (bacilli Calmette-Guerin); *Corynebacterium parvum*; saponins purified from the bark of the *Quillija saponaria* tree, such as QS-21 (a glycolipid that elutes in the $21^{st}$ peak with HPLC fractionation; Agenus, Inc., Lexington, Mass.); polyphosphazenes such as poly[di(carboxylatophenoxy) phosphazene] (PCPP polymer; Celldex Therapeutics, Inc., Needham, Mass.); derivatives of lipopolysaccharides such as monophosphoryl lipid A (MPL®; GlaxoSmithKline, Philadelphia, Pa.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; GlaxoSmithKline, Philadelphia, Pa.), emulsion-based formulations including mineral oil, non-mineral oil, water-in-oil or oil-in-water-in oil emulsion, oil-in-water emulsions such as Seppic ISA series of Montanide adjuvants; and PROVAX, ISCOMs (Immunostimulating complexes which contain mixed saponins, lipids and form virus-sized particles with pores that can hold antigen; SB-AS2 (SmithKline Beecham adjuvant system #2 which is an oil-in-water emulsion containing MPL and QS21: SmithKline Beecham Biologicals [SBB], Rixensart, Belgium); SB-AS4 (SmithKline Beecham adjuvant system #4 which contains alum and MPL; SBB, Belgium); non-ionic block copolymers that form micelles such as CRL 1005 (these contain a linear chain of hydrophobic polyoxypropylene flanked by chains of polyoxyethylene; Vaxcel, Inc., Norcross, Ga.); and Syntex Adjuvant Formulation (SAF, an oil-in-water emulsion containing Tween 80 and a nonionic block copolymer; Syntex Chemicals, Inc., Boulder, Colo.).

Immunogenic compositions may be sterilized by conventional, well known sterilization techniques, or may be sterile filtered.

The immunogenic compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, among many others.

Administration of Immunogenic PND Compositions as Vaccines

Methods of administrating immunogenic compositions to a subject are provided. As used herein, the term "subject" refers to any animal including, but not limited to, humans, non-human primates, rodents, and the like. Typically, the terms "subject" and "patient" are used interchangeably herein in reference to a human subject. The immunogenic compositions induce an immune response in the subject to the immunogen in the compositions. As used herein, the terms "administration" and "administering" refer to the act of giving a composition of the present disclosure to a subject. Exemplary routes of administration include ophthalmic, oral, transdermal, subcutaneous, intranasal, pulmonary, buccal, oral, rectal, intravenous, subcutaneous, intraperitoneal, intramuscular or topical routes.

As used herein, the terms "co-administration" and "co-administering" refer to the administration of at least two agent(s), an immunogenic composition disclosed herein and one or more other agents or therapies to a subject. In some embodiments, the co-administration of two or more agents or therapies is concurrent. In other embodiments, a first agent/therapy is administered prior to a second agent/therapy. In some embodiments, co-administration can be via the same or different route of administration. Those of skill in the art understand that the formulations and/or routes of administration of the various agents or therapies used may vary. As one example, co-administration can elicit an immune response in a subject to two or more different immunogens.

The dose of the immunogenic compositions may vary over a range from about 0.001 to about 1,000 mg of immunogen. In some embodiments, the dose is about 0.0001 mg/kg to about 50 mg/kg of body weight per dose. In some embodiments, the dose is about 0.0001 mg/kg to about 7 mg/kg of body weight per dose.

In some embodiments, the immunogenic compositions described herein are administered to a subject by injection. In some embodiments, the immunogenic compositions are injected intradermally, subcutaneously, or intramuscularly to allow for uptake by, or exposure to, antigen presenting cells located in the skin, epidermis or dermis.

In some embodiments, an initial dose of immunogenic composition is followed by booster doses, following immunization protocols standard in the art, and their effect may be potentiated by adjuvants or cytokines well known to those skilled in the art.

As used herein, the terms "a composition for inducing an immune response," "immunogenic composition" or grammatical equivalents refer to a composition that, once administered to a subject stimulates, generates and/or elicits an immune response in the subject resulting in total or partial immunity to *S. aureus*. An immune response may be an innate (e.g., a non-specific) immune response or a learned (e.g., acquired) immune response (e.g. that decreases the infectivity, morbidity, or onset of mortality in a subject, or that prevents infectivity, morbidity, or onset of mortality in a subject. In some embodiments, an immunogenic composition described herein is administered to a subject as a vaccine to prevent or attenuate a disease by providing to the subject total or partial immunity against *S. aureus* causing the disease or by providing the total or partial attenuation of a symptom or sequelae of the disease.

A used herein, the term "immune response" refers to a response by the immune system of a subject. For example, immune responses include, but are not limited to, a detectable alteration (e.g., increase) in Toll receptor activation, lymphokine (e.g., a cytokine such as Th1 or Th2 type cytokines, or chemokine) expression and/or secretion, macrophage activation, dendritic cell activation, T cell activation (e.g., CD4+ or CD8+ T cells), NK cell activation, and/or B cell activation (e.g., antibody generation and/or secretion). Additional examples of immune responses include binding of an immunogen to an MHC molecule and inducing a cytotoxic T lymphocyte ("CTL") response, inducing a B cell response (e.g., antibody production), and/or T-helper lymphocyte response, and/or a delayed type hypersensitivity (DTH) response against the antigen from which the immunogen is derived, expansion (e.g., growth of a population of cells) of cells of the immune system (e.g., T cells, B cells (e.g., of any stage of development (e.g., plasma cells), and increased processing and presentation of antigen by antigen presenting cells. An immune response may be to immunogens that the subject's immune system recognizes as foreign (e.g., non-self antigens from microorganisms (e.g., pathogens), or self-antigens recognized as foreign). Thus, it is to be understood that, as used herein, "immune response" refers to any type of immune response, including, but not limited to, innate immune responses (e.g., activation of Toll receptor signaling cascade) cell-mediated immune responses (e.g., responses mediated by T cells (e.g., antigen-specific T cells) and non-specific cells of the immune system) and humoral immune responses (e.g., responses mediated by B cells (e.g., via generation and secretion of antibodies into the plasma, lymph, and/or tissue fluids). The term "immune response" is meant to encompass one or more of all the possible aspects of the capability of a subject's immune system to respond to immunogens (e.g., both the initial response to an immunogen (e.g., a pathogen) as well as acquired (e.g., memory) responses that are a result of an adaptive immune response).

As used herein, the term "immunity" refers to protection from disease (e.g., preventing or attenuating of a sign, symptom or condition of the disease) upon exposure to a microorganism (e.g., pathogen) capable of causing the disease. Immunity can be innate (e.g., non-adaptive, non-acquired immune responses that exist in the absence of a previous exposure to an antigen) and/or acquired (e.g., immune responses that are mediated by B and T cells following a previous exposure to antigen (e.g., that exhibit increased specificity and reactivity to the antigen)). The term "enhanced immunity" refers to an increase in the level of adaptive and/or acquired immunity in a subject to a given immunogen (e.g., microorganism (e.g., pathogen)) following administration of an immunogenic composition relative to the level of adaptive and/or acquired immunity in a subject that has not been administered the immunogenic composition (e.g., composition for inducing an immune response of the present disclosure).

As used herein, the term "an effective amount" of an immunogenic composition refers to an amount administered in methods that is effective to induce an immune response in the subject. An effective amount can be administered in one or more doses administered via the same or different route.

In alternative embodiments of administration of immunogens described herein, polynucleotides (DNA or RNA, each including any appropriate control sequences) encoding the immunogens can be administered to a subject. The polynucleotide may be administered as naked DNA or in a delivery vehicle known in the art including, but not limited to, a viral vector (such as a adeno-associated virus or lentivirus vector), or a lipid-based, polymer-based or nanoparticle-based complex.

PND-Specific Antibody Products

PND-specific antibody products are provided herein. In some embodiments, the PND-specific antibody is the rabbit monoclonal antibody named 3G6. Other PND-specific antibody products can be produced by methods standard in the art, some of which are described in the following paragraphs.

As used herein, the term "antibody" refers to a tetrameric immunoglobulin composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

In some embodiments, the antibody products comprise 3G6 mAb the heavy chain variable region set out in SEQ ID NO: 8 and the 3G6 mAb light chain variable region set out SEQ ID NO: 9. Some antibody products that are provided comprise a heavy chain variable region and/or a light chain variable region comprising a sequence of amino acids that differ(s) from the sequence of the 3G6 heavy chain variable region and/or the 3G6 light chain variable region at only 1, 2, 3, 4, 5, 6, 7, 8, 9, 10, 11, 12, 13, 14 or 15 amino acid residues, wherein each such sequence difference is independently either a deletion, insertion or substitution of one amino acid. The light and heavy chain variable regions, in some antigen binding proteins, comprise sequences of amino acids that have at least 70%, 75%, 80%, 85%, 90%, 91%, 92%, 93%, 94%, 95%, 96%, 97%, 98% or 99% sequence identity to the 3G6 amino acid sequences. Still other antibody products also include variant heavy chain region forms and/or variant light chain region forms as described herein.

As used herein, "antibody fragments" comprise a portion of a tetrameric immunoglobulin. Examples of antibody fragments include Fab, Fab', F(ab')$_2$, and Fv fragments. There are a number of well-characterized antibody fragments that are produced by digestion with various peptidases. Thus, for example, pepsin digests an antibody below the disulfide linkages in the hinge region to produce F(ab')$_2$, a dimer of Fab which itself is a light chain joined to $V_H$-CH1 by a disulfide bond. The F(ab')$_2$ may be reduced under mild conditions to break the disulfide linkage in the hinge region thereby converting the (Fab')$_2$ dimer into an Fab' monomer. The Fab' monomer is essentially an Fab with part of the hinge region (see, Fundamental Immunology, W. E. Paul, ed., Raven Press, N.Y. (2012), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology.

An "antigen-binding site" or "binding portion" refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs." Numbering systems have been devised for assigning numbers to amino acids that occupy positions in each of these regions. Complementarity determining regions and framework regions of a given antigen binding protein may be identified using these systems. Numbering systems are defined in Kabat et al., Sequences of Proteins of Immunological Interest, 5.sup.th Ed., US Dept. of Health and Human Services, PHS, NIH, NIH Publication No. 91-3242, 1991, or Chothia & Lesk, 1987, J. Mol. Biol. 196:901-917; Chothia et al., 1989, Nature 342:878-883. Other numbering systems for the amino acids in immunoglobulin chains include IMGT® (the international ImMunoGeneTics information system; Lefranc et al, Dev. Comp. Immunol. 2005, 29:185-203); and AHo (Honegger and Pluckthun, J. Mol. Biol. 2001, 309(3): 657-670). The CDRs provided herein may not only be used to define the antigen binding domain of a traditional antibody structure, but may be embedded in a variety of other antibody product structures, as described herein. In some embodiments, the antibody products comprise the 3G6 mAb heavy chain CDRs set out in SEQ ID NOs: 2, 3 and 4 and the 3G6 mAb light chain CDRs set out in SEQ ID NO: 5, 6 and 7. In some embodiments, the CDRs in an antibody product comprise sequences of amino acids that have at least 80%, 85%, 90%, 91%, 92, 93%, 94%, 95%, 96%, 97%, 98%, or 99% sequence identity to 3G6 mAb CDRs.

The term "antibody product" is used herein to refer to whole antibodies, monoclonal antibodies (including human, humanized, or chimeric antibodies), polyclonal antibodies, and antibody fragments that can bind antigen (e.g., Fab', F' (ab).sub.2, Fv, single chain antibodies), comprising complementarity determining regions (CDRs) of the foregoing as long as they exhibit the desired biological activity.

When an immunogen is used to immunize a host animal, regions of the immunogen induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody product.

The term "antigenic determinant" or "epitope" thus refers to a site on an antigen to which an antibody product binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. Epitope determinants may include chemically active surface groupings of molecules such as amino acids, sugar side chains, phosphoryl or sulfonyl groups, and may have specific three dimensional structural characteristics, and/or specific charge characteristics. An epitope typically includes at least 3, 4, 5, 6, 7, 8, 9, 10, 11, 12, 13, 14, 15, 16, 17, 18, 19, 20, 25, 30, 35 amino acids in a unique spatial conformation. Epitopes can be determined using methods known in the art.

An antibody product that "specifically binds to" or is "specific for" a particular polypeptide or an epitope on a particular polypeptide is one that binds to that particular polypeptide or epitope on a particular polypeptide without substantially binding to any other polypeptide or polypeptide epitope. See Harlow and Lane (1988) Antibodies, A Laboratory Manual, Cold Spring Harbor Publications, New York, for a description of immunoassay formats and conditions that can be used to determine specific immunoreactivity.

As used herein, the terms "immunological binding" and "immunological binding properties" refer to the non-covalent interactions of the type which occur between an antibody product and an antigen for which the antibody product is specific. The strength or affinity of immunological binding interactions can be expressed in terms of the dissociation constant (Kd) of the interaction, wherein a smaller Kd represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity and is thus equal to the dissociation constant Kd. See, generally, Davies et al. *Ann. Rev. Biochem.*, 59: 439-473 (1990).

Monoclonal antibodies that specifically bind to the AT PND can be prepared using any technique which provides for the production of antibody molecules by continuous cell lines in culture. These techniques include, but are not limited to, the hybridoma technique, the human B cell hybridoma technique, and the EBV hybridoma technique (See, e.g., Kohler et al., *Nature,* 256: 495-497 (1985); Kozbor et al., *J. Immunol. Methods,* 81: 3142 (1985); Cote et al., *Proc. Natl. Acad. Sci.,* 80: 2026-2030 (1983); Cole et al., *Mol. Cell. Biol.,* 62: 109-120 (1984). Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XXO Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6. In some instances, a hybridoma cell line is produced by immunizing an animal (e.g., a transgenic animal having human immunoglobulin sequences) with the AT PND; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that specifically binds the AT PND.

A chimeric antibody is a molecule in which different portions of an antibody are derived from different immunoglobulin molecules. Methods for producing chimeric antibodies are known in the art. See e.g., Morrison, *Science*, 229: 1202 (1985); Oi et al., *BioTechniques*, 4: 214 (1986); Gillies et al., *J. Immunol. Methods*, 125: 191-202 (1989); and U.S. Pat. Nos. 5,807,715, 4,816,567, 4,816,397, and 6,311,415.

A humanized antibody is an antibody or its variant or fragment thereof which is capable of binding to a predetermined antigen and which comprises a framework region having substantially the amino acid sequence of a human immunoglobulin and a CDR having substantially the amino acid sequence of a non-human immuoglobulin. A humanized antibody comprises substantially all of at least one, and typically two, variable domains (Fab, Fab', F(ab')$_2$, Fabc, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including IgG1, IgG2, IgG3 and IgG4. Usually the constant domain is a complement fixing constant domain where it is desired that the humanized antibody exhibit cytotoxic activity, and the class is typically IgG$_1$. Where such cytotoxic activity is not desirable, the constant domain may be of the IgG$_2$ class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental framework region (FR) and CDR sequences, more often 90%, and most preferably greater than 95%. Humanized antibody can be produced using variety of techniques known in the art, including but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, *Molecular Immunology*, 28(4/5): 489-498 (1991); Studnicka et al., *Protein Engineering* 7(6): 805-814 (1994); and Roguska et al., *PNAS*, 91: 969-973 (1994), chain shuffling (U.S. Pat. No. 5,565,332), and techniques disclosed in, e.g., U.S. Pat. No. 6,407,213, U.S. Pat. No. 5,766,886, WO 9317105, Tan et al., *J. Immunol.*, 169: 1119-25 (2002), Caldas et al., *Protein Eng.*, 13(5): 353-60 (2000), Morea et al., *Methods*, 20(3): 267-79 (2000), Baca et al., *J. Biol. Chem.*, 272(16): 10678-84 (1997), Roguska et al, *Protein Eng.*, 9(10): 895-904 (1996), Couto et al., *Cancer Res.*, 55 (23 Supp): 5973s-5977s (1995), Couto et al., *Cancer Res.*, 55(8): 1717-22 (1995), Sandhu, *Gene*, 150(2): 409-10 (1994), and Pedersen et al., *J. Mol. Biol.*, 235(3): 959-73 (1994). Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., *Nature*, 332: 323 (1988).

Fully human antibodies can be produced by immunizing transgenic animals (usually mice) that are capable of producing a repertoire of human antibodies in the absence of endogenous immunoglobulin production. Antigens for this purpose typically have six or more contiguous amino acids, and optionally are conjugated to a carrier, such as a hapten. See, e.g., Jakobovits et al., *Proc. Natl. Acad. Sci. USA*, 90: 2551-2555 (1993); Jakobovits et al., *Nature*, 362: 255-258 (1993); and Bruggermann et al., *Year in Immunol.*, 7: 33 (1993). In one example of such a method, transgenic animals are produced by incapacitating the endogenous mouse immunoglobulin loci encoding the mouse heavy and light immunoglobulin chains therein, and inserting into the mouse genome large fragments of human genome DNA containing loci that encode human heavy and light chain proteins. Partially modified animals, which have less than the full complement of human immunoglobulin loci, are then crossbred to obtain an animal having all of the desired immune system modifications. When administered an immunogen, these transgenic animals produce antibodies that are immunospecific for the immunogen but have human rather than murine amino acid sequences, including the variable regions. For further details of such methods, see, for example, WIPO patent publications WO96/33735 and WO94/02602. Additional methods relating to transgenic mice for making human antibodies are described in U.S. Pat. Nos. 5,545,807; 6,713,610; 6,673,986; 6,162,963; 5,545,807; 6,300,129; 6,255,458; 5,877,397; 5,874,299 and 5,545,806; in WIPO patent publications WO91/10741, WO90/04036, and in EP 546073B1 and EP 546073A1.

The transgenic mice described in the foregoing paragraph contain a human immunoglobulin gene minilocus that encodes unrearranged human heavy ([mu] and [gamma]) and [kappa] light chain immunoglobulin sequences, together with targeted mutations that inactivate the endogenous [mu] and [kappa] chain loci (Lonberg et al., *Nature*, 368: 856-859 (1994). Accordingly, the mice exhibit reduced expression of mouse IgM or [kappa] and in response to immunization, and the introduced human heavy and light chain transgenes undergo class switching and somatic mutation to generate high affinity human IgG [kappa] monoclonal antibodies. Technologies utilized for producing human antibodies in these transgenic mice are disclosed also in WIPO Publication No. WO 98/24893, and Mendez et al., *Nature Genetics*, 15: 146-156 (1997). For example, the HCo7 and HCo12 transgenic mice strains can be used to generate PND-specific human antibodies. Using hybridoma technology, antigen-specific human mAbs with the desired specificity can be produced and selected from the transgenic mice such as those described above. Such antibodies may be cloned and expressed using a suitable vector and host cell, or the antibodies can be harvested from cultured hybridoma cells.

Fully human antibodies can also be derived from phage-display libraries [such as disclosed in Hoogenboom et al., J. Mol. Biol., 227: 381 (1991); Marks et al., J. Mol. Biol., 222: 581 (1991); WIPO Publication No. WO 99/10494]. Phage display techniques mimic immune selection through the display of antibody repertoires on the surface of filamentous bacteriophage, and subsequent selection of phage by their binding to an antigen of choice.

Single chain antibodies which specifically bind to a particular antigen can be produced. For example, single-chain antibodies can be constructed using a DNA amplification method, such as PCR, using hybridoma cDNA as a template (See, e.g., Thirion et al., *Eur. J. Cancer Prev.*, 5: 507-511 (1996). Single-chain antibodies can be mono- or bispecific, and can be bivalent or tetravalent. Construction of tetravalent, bispecific single-chain antibodies is taught, for example, in Coloma and Morrison, *Nat. Biotechnol.*, 15: 159-163 (1997). Construction of bivalent, bispecific single-chain antibodies is taught, for example, in Mallender and Voss, *J. Biol. Chem.*, 269: 199-206 (1994). A nucleotide sequence encoding a single-chain antibody can be constructed using manual or automated nucleotide synthesis, cloned into an expression construct using standard recombinant DNA methods, and introduced into a cell to express the coding sequence. Alternatively, single-chain antibodies can be produced directly using, for example, filamentous phage technology (See, e.g., Verhaar et al., *Int. J. Cancer*, 61: 497-501 (1995); Nicholls et al., *J. Immunol. Meth.*, 165: 81-91 (1993).

Antibody products that are multivalent and multispecific can also be prepared. Domain antibodies are immunologically functional immunoglobulin fragments containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens. Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., *Proc. Natl. Acad. Sci. USA*, 90: 6444-6448 (1993) and Poljak et al., *Structure*, 2: 1121-23 (1994). Similarly, tribodies and tetrabodies are antibodies comprising three and four polypeptide chains, respectively, and forming three and four antigen binding sites, respectively, which can be the same or different. Maxibodies comprise bivalent scFvs covalently attached to the Fc region of IgG1, (see, e.g., Fredericks et al, *Protein Engineering, Design & Selection*, 17: 95-106 (2004); Powers et al., *Journal of Immunological Methods*, 251: 123-135 (2001); Shu et al., *Proc. Natl. Acad. Sci. USA*, 90: 7995-7999 (1993); Hayden et al., *Therapeutic Immunology* 1: 3-15 (1994).

The term "compete" when used in the context of antibody products means competition between antibody products as determined by an assay in which the antibody product being tested prevents or inhibits specific binding of a reference protein (e.g., a ligand, or a reference antibody product) to a common antigen (e.g., the AT PND). Numerous types of competitive binding assays can be used, for example: solid phase direct or indirect radioimmunoassay (RIA), solid phase direct or indirect enzyme immunoassay (EIA), sandwich competition assay (see, e.g., Stahli et al., *Methods in Enzymology*, 92: 242-253 (1983); solid phase direct biotin-avidin EIA (see, e.g., Kirkland et al., *J. Immunol.*, 137: 3614-3619 (1986), solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., *Mol. Immunol.*, 25: 7-15 (1988); solid phase direct biotin-avidin EIA (see, e.g., Cheung, et al., *Virology*, 176: 546-552 (1990); and direct labeled RIA (Moldenhauer et al., *Scand. J. Immunol.*, 32: 77-82 (1990).

Competitive inhibition is measured by determining the amount of label bound to the solid surface or cells in the presence of the test antibody product. Usually the test antibody product is present in excess. Antibody products identified by competition assay (competing antibody products) include antibody products binding to the same epitope as the reference antibody products and antibody products binding to an adjacent epitope sufficiently proximal to the epitope bound by the reference antibody products for steric hindrance to occur. Usually, when a competing antibody product is present in excess, it will inhibit specific binding of a reference antibody product to a common antigen by at least 40%, 45%, 50%, 55%, 60%, 65%, 70% or 75%. In some instance, binding is inhibited by at least 80%, 85%, 90%, 91%, 92%, 93%, 94%, 95%, 96%, 97% 98%, 99% or more.

Recombinant expression of an antibody product described herein involves construction of an expression vector containing a polynucleotide that encodes the antibody. Once a polynucleotide encoding an antibody product has been obtained, the vector for the production of the antibody molecule may be produced by recombinant DNA technology using techniques well-known in the art. See, e.g., U.S. Pat. No. 6,331,415. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The disclosure, thus, provides replicable vectors comprising a nucleotide sequence encoding an antibody product operably linked to a promoter. The expression vector is transferred to a host cell by conventional techniques and the transfected cells are then cultured by conventional techniques to produce the antibody product. Thus, the disclosure includes host cells containing a polynucleotide or polynucleotides encoding the antibody product operably linked to a heterologous promoter. In preferred embodiments for the expression of double-chained antibodies, vectors encoding both the heavy and light chains may be co-expressed in the host cell for expression of the entire immunoglobulin molecule, as detailed below. A variety of host-expression vector systems may be utilized to express the antibody products described herein (see, e.g., U.S. Pat. No. 5,807,715). The expression levels of an antibody product can be increased by vector amplification [for a review, see Bebbington and Hentschel, The use of vectors based on gene amplification for the expression of cloned genes in mammalian cells in DNA cloning, Vol. 3. (Academic Press, New York, 1987)]. The host cell may be co-transfected with two expression vectors, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, Nature 322: 52; and Kohler, 1980, Proc. Natl. Acad. Sci. USA 77: 2 197). The coding sequences for the heavy and light chains may comprise cDNA or genomic DNA.

Antibody products may be purified by any method known in the art for purification of an immunoglobulin molecule, for example, by chromatography (e.g., ion exchange, affinity, particularly by affinity for the specific antigen after Protein A and sizing column chromatography), centrifugation, differential solubility, or by any other standard technique for the purification of proteins. Further, the antibody products may be fused to heterologous polypeptide sequences described herein or otherwise known in the art to facilitate purification.

Antibody products described herein totally or partially reduce, inhibit, interfere with or modulate one or more biological activities of S. aureus AT. Such inhibition or neutralization disrupts a biological activity in the presence of the antibody product compared to the response in the absence of the antibody product. Such comparisons may be demonstrated in vitro through the prevention or reduction of the effects of AT on red blood cells or nucleated cells. This may be demonstrated through use of an indicator of cell viability in assays known to one skilled in the art. Such comparisons may also take the form of preventing or reducing the effect of AT in vivo, resulting either from the administration of AT or S. aureus producing AT, through assessment of pathology and/or survival employing protocols known to one skilled in the art. Reduction of biological activity can be about 20%, 30%, 40%, 50%, 60%, 70%, 80%, 85%, 90%, 91%, 92%, 93%, 94%, 95%, 96%, 97% 98%, 99% or more.

Antibody products having a half-life of at least one day in vitro or in vivo (e.g., when administered to a human subject) are provided. In some embodiments, the half-life is at least three days. In some embodiments, the half-life is four days or longer. In some embodiments, the half-life is eight days or longer. In some embodiments, antibody product is derivatized or modified such that it has a longer half-life as compared to the underivatized or unmodified antibody product. In another embodiment, the antibody product contains point mutations to increase serum half life, such as described in WIPO Publication No. WO 00/09560.

Compositions comprising PND-specific antibody products are provided. Compositions comprise one or more additional components such as a physiologically acceptable carrier. A pharmaceutical composition may comprise an PND-specific antibody product together with one or more substances selected from the group consisting of a buffer, an antioxidant such as ascorbic acid, a low molecular weight polypeptide (such as those having fewer than ten amino acids), a protein, an amino acid, a carbohydrate such as glucose, sucrose or dextrins, a chelating agent such as EDTA, glutathione, a stabilizer, and an excipient. Neutral buffered saline or saline mixed with conspecific serum albumin are examples of appropriate diluents. In accordance with appropriate industry standards, preservatives such as benzyl alcohol may also be added. The composition may be formulated as a lyophilizate using appropriate excipient solutions (e.g., sucrose) as diluents. Suitable components are nontoxic to recipients at the dosages and concentrations employed. Further examples of components that may be employed in pharmaceutical formulations are presented in any Remington's Pharmaceutical Sciences including the 21$^{st}$ Ed. (2005), Mack Publishing Company, Easton, Pa.

Administration of PND-Specific Antibody Products to Treat S. Aureus Infections

Methods of administration of PND-specific antibody products to treat S. aureus infection are provided.

As use herein, "treating" or "treatment" of S. aureus infection includes prophylactically or therapeutically: preventing or delaying the appearance of at least one clinical or sub-clinical symptom of the infection; inhibiting the progression of the infection or relieving the infection or at least one of its clinical or sub-clinical symptoms. The benefit to a subject to be treated is statistically significant or at least perceptible to the patient or to the physician.

As defined herein, an "effective" amount of an antibody product (i.e., an effective dose) means an amount sufficient to produce a clinically desirable result. Doses and the frequency of administration may vary according to such factors as the route of administration, the particular antibody product employed, the nature and severity of the infection to be treated, and the size and general condition of the subject. Appropriate doses can be determined by procedures known in the pertinent art, e.g. in clinical trials that may involve dose escalation studies.

A typical dose may range from about 0.1 μg/kg to up to about 30 mg/kg or more, depending on the factors mentioned above. In some embodiments, the dose may range from 0.1 μg/kg up to about 30 mg/kg, optionally from 1.mu.g/kg up to about 30 mg/kg, optionally from 10.mu.g/kg up to about 10 mg/kg, optionally from about 0.1 mg/kg to 5 mg/kg, or optionally from about 0.3 mg/kg to 3 mg/kg.

Dosing frequency will depend upon the pharmacokinetic parameters of the particular antibody product in the composition. Typically, a clinician administers the composition until a dose is reached that achieves the desired effect. The composition may therefore be administered as a single dose, or as two or more doses (which may or may not contain the same amount of the desired molecule) over time, or as a continuous infusion via an implantation device or catheter. Appropriate dosages may be ascertained through use of appropriate dose-response data. An antibody product described herein may be administered once or more than once, e.g., at regular intervals over a period of time. In particular embodiments, an antibody product is administered over a period of at least a month or more, e.g., for one, two, or three months or even indefinitely. In general, the antibody product is administered until the patient manifests a medically relevant degree of improvement over baseline for the chosen indicator or indicators.

In some embodiments, an antibody product composition described herein is co-administered with one or more antibiotics. For example, one or more antibiotics may be administered with, before and/or after administration of an antibody product composition. The present disclosure is not limited by the type of antibiotic co-administered. Indeed, a variety of antibiotics may be co-administered including, but not limited to, β-lactam antibiotics, penicillins (such as natural penicillins, aminopenicillins, penicillinase-resistant penicillins, carboxy penicillins, ureido penicillins), cephalosporins (first generation, second generation, and third generation cephalosporins), and other β-lactams (such as imipenem, monobactams), β-lactamase inhibitors, vancomycin, linezolid, daptomycin, tigecycline, telavancin, dalbavancin, oritavancin, aminoglycosides and spectinomycin, tetracyclines, chloramphenicol, erythromycin, lincomycin, clindamycin, minocycline, trimethoprim-sulfamethoxazole, rifampin, metronidazole, polymyxins, doxycycline, quinolones (e.g., ciprofloxacin), sulfonamides, trimethoprim, ceftobiprole, mupirocin and/or iclaprim.

In some embodiments, an antibody product composition described herein is co-administered with one or more antimicrobial agents. There are many antimicrobial agents currently available for use in treating bacterial, fungal and viral infections. For a comprehensive treatise on the general classes of such drugs and their mechanisms of action, the skilled artisan is referred to Goodman & Gilman's "The Pharmacological Basis of Therapeutics" Eds. Hardman et al., 9th Edition, Pub. McGraw Hill, chapters 43 through 50, 1996.

Kits for use by medical practitioners are provided and include an antibody product described herein and a label or other instructions for use in treating S. aureus infections.

A finished, packaged and labeled pharmaceutical product is also provided. Such an article of manufacture includes an appropriate unit dosage form in an appropriate vessel or container such as a glass vial or other container that is hermetically sealed. In the case of dosage forms suitable for parenteral administration the active ingredient is sterile and suitable for administration as a particulate free solution. Both parenteral solutions and lyophilized powders are provided, each being sterile, and the latter being suitable for reconstitution prior to injection. In some embodiments, the unit dosage form is suitable for intravenous, intramuscular or subcutaneous delivery.

In some embodiments, compositions are stored in containers with biocompatible detergents, including but not limited to, lecithin, taurocholic acid, and cholesterol; or with other proteins, including but not limited to, gamma globulins and serum albumins. As with any pharmaceutical product, the packaging material and container are designed to protect the stability of the compositions during storage and shipment.

More specifically, articles of manufacture are provided that comprise packaging material, such as a box, bottle, tube, vial, container, sprayer, insufflator, intravenous (i.v.) bag, envelope and the like; and at least one unit dosage form of a composition contained within said packaging material. Also provided are articles of manufacture comprising packaging material, such as a box, bottle, tube, vial, container, sprayer, insufflator, intravenous (i.v.) bag, envelope and the like; and at least one unit dosage form of each composition contained within said packaging material. Also provided are articles of manufacture comprising packaging material, such as a box, bottle, tube, vial, container, sprayer, insufflator, intravenous (i.v.) bag, envelope and the like; and at least one unit dosage form of each composition contained within said packaging material. An article of manufacture may also comprise a needle or syringe, preferably packaged in sterile form, for injection of the formulation, and/or a packaged alcohol pad.

In some embodiments, rather than administering an antibody product to a patient to treat S. aureus infection, a polynucleotide (DNA or RNA, each including any appropriate control sequences) encoding the antibody product is administered to the patient. The polynucleotide may be administered in a delivery vehicle known in the art including, but not limited to, a viral vector (such as a adeno-associated virus or lentivirus vector), or a lipid-based, polymer-based or nanoparticle-based complex.

EXAMPLES

Like the protective antigen (PA) from B. anthracis, S. aureus AT is a member of a class of β-barrel pore forming toxins, a group which also includes the leukotoxins of S. aureus, but also members that multimerize to form larger pores, such as streptolysin O, aerolysin, Clostridium perfringens perfringolysin O, among other toxins [Song et al., Science, 274: 1859-1866 (1996); reviewed in Gonzalez et al., Cell. Mol. Life Sci., 65: 493-507 (2008)]. These toxins all employ a β-loop structure to cross the membrane in the assembled pore.

We previously determined that a linear determinant in the 2β2-2β3 loop in the pore forming domain of B. anthracis PA, a key member of the protein complex that ultimately leads to formation of lethal toxin, the virulence factor responsible for the tissue injury and lethality of aerosolized anthrax, is a potent neutralizing epitope. Immunization with multiple antigenic peptides (MAPs) targeting this sequence, known as the loop neutralizing determinant (LND), elicits antibody capable of highly potent neutralization in vitro and protection of rabbits from a 200 $LD_{50}$ aerosol challenge with the highly virulent B. anthracis Ames strain in vivo [Oscherwitz et al., Clin. Vaccine Immunol., 20: 341-349 (2013); Oscherwitz et al., J. Immunol., 185: 3661-3668 (2010)]. Interestingly, the LND is immunologically silent in rabbits and non-human primates immunized with whole PA, and more recently we determined in collaboration with the CDC, that antibodies to the LND are undetectable in sera from a large cohort of human vaccinees who received AVA, the approved vaccine for anthrax, which contains PA as the primary immunogenic component. [Oscherwitz et al., Infect. Immun., 77: 5509-5518 (2009); Oscherwitz et al., J. Immunol., 185: 3661-3668 (2010); Oscherwitz et al., Infect. Immun., 77: 3380-3388 (2009)].

Our recognition of the structural and functional similarities of AT and PA led us to examine whether AT, like PA, might contain an important neutralizing epitope in the region of AT analogous to the 2β2-2β3 loop of PA where the LND is found. The linear nature of the LND, and the potency of antibodies against this site for in vitro toxin neutralization and ultimately, protection of rabbits from lethal aerosol spore challenge with B. anthracis Ames strain, are qualities contemplated herein to be highly desirable for a neutralizing epitope against AT for inclusion in a mono- or multivalent vaccine against S. aureus.

The examples below show that an S. aureus pore neutralizing determinant herein designated "PND" is a highly promising antibody target for neutralization of AT. Passive immunization of mice with affinity purified, polyclonal rabbit antibody elicited to epitope-specific immunogens targeting the PND is highly effective at mediating protection from dermonecrosis with either a MSSA strain (8325-4) or a MRSA strain (LAC/USA300) of S. aureus. Moreover, like the LND, in experiments described below the PND is immunorecessive in rabbits immunized with full length AT, as no detectable antibody can be found that is immunoreactive with PND peptides.

Various aspects and embodiments of the invention are illustrated by the following non-limiting examples.

Materials and Methods Used in the Examples

Synthetic Peptides

MAPs and linear synthetic peptides used in this study were synthesized commercially (Bio-Synthesis, Inc., Lewisville Tex.). The sequences of the candidate B cell epitope segments are listed in FIG. 5. Linear synthetic peptides were HPLC purified to greater than 90% purity and included the peptides, amino acids 1-19 and amino acids 122-137 from alpha hemolysin (UniProtKB P09616). For all studies employing MAPs, 4-branch constructs were synthesized with the respective AT B cell sequence positioned at the C-terminus, colinearly synthesized with the T* helper T cell epitope (EYLNKIQNSLSTEWSPCSVT) (SEQ ID NO: 11) at the N-terminus as employed previously [Oscherwitz (2010), supra; Moreno et al., Int. Immunol., 3: 997-1003 (1991)]. For some studies, rabbits were immunized with a mixture containing MAPS synthesized with T* helper epitope as well as separately with the P30 helper T cell epitope (FNNFTVSFWLRVPKVSASHLE) (SEQ ID NO: 12) from tetanus toxin at the N-terminus as described [Oscherwitz et al., *Infect. Immun.*, 77: 5509-5518 (2009); Panina-Bordignon et al., *Eur. J. Immunol.*, 19: 2237-2242 (1989)]. Control MAPs used for this study consisted of 4-branch constructs with the T* and P30 helper epitopes separately linked to a B cell sequence (QSVEINC-TRPNNNTRKSIHMGPGRAF) (SEQ ID NO: 13) derived from V3 loop sequences of HIV-1. Structural examination and comparison of 3-dimensional structures employed experimental and modeled structures available through the Protein Data Bank (rcsb.org), typically using the PyMOL Molecular Graphic System, version 1.6 (Schrödinger, LLC). Primary structure was studied using ClustalX version 2.1.

Animals and Vaccinations

Approximately 6-12 week old female C57BL/6 and BALB/c mice (Charles River, Portage Mich.) were used for the mouse experiments. Passive immunization was performed as described in text with either rabbit antisera or affinity purified rabbit IgG. Rabbit antisera were purified on Protein A according the manufacturers protocol, sterile filtered, and adjusted to a concentration of approximately 1 mg/ml for use in passive transfer studies (Thermo Fisher Scientific Inc., Rockford Ill.). For procurement of rabbit antisera, female New Zealand white (NZW) rabbits (Covance Research Products, Denver, Pa.) were immunized on day 0 with 250 µg of the respective MAP immunogens in an emulsion with CFA and were then boosted 3 times at two-week intervals with 125 µg of the respective MAP in an emulsion with IFA. For assessment of antibody responses, rabbits were bled 10-14 days after the final immunization. Mice and rabbits were cared for in accordance with the standards of the Association for Assessment and Accreditation of Laboratory Animal Care, and all animal procedures were approved by the Institutional Animal Care and Use Committee.

Bacterial Strains

*S. aureus* strain 8325-4, and the isogenic hla(−) deletion mutant are MSSA strains that have been described previously and were kindly provided by Dr. Timothy Foster (Trinity College, Dublin, Ireland) [Bartlett et al., *J. Infect. Dis.*, 198: 1529-1535 (2008)]. The MRSA strain LAC/USA300 was kindly provided by Dr. Michael Otto (NIH, Bethesda, Md.) and by Dr. Juliane Bubeck Wardenburg (U. of Chicago). These USA300 strains were found to be indistinguishable; for consistency, the LAC/USA300 from Dr. Otto was used throughout the present study. Strain SAP149 which was generously provided by Dr. Scott Stibitz (NIH), is a luminescent derivative of NRS384 and has been described elsewhere [Prabhakara et al., *Infect. Immun.*, 81: 1306-1315 (2013); Plaut et al., *PLoS One*, 8: e59232 (2013)].

Preparation of Bacteria for Dermonecrosis Challenge Model

For preparation of challenge stocks, *S. aureus* strains were grown overnight (ON) (Day 0) in trypic soy broth (TSB, Sigma Biochemicals, St. Louis, Mo.) at 37° C. with shaking at 230 rpm in 200 ml Erlenmeyer flasks. For strain SAP149 only, cultures were supplemented with 10 µg/ml of chloramphenicol (Sigma Biochemicals). ON cultures were were diluted 1:100 (Day 1) and were expanded for 3 hours at 37° C. and 230 rpm until mid-exponential phase (approximately 0.7 OD at 600 nm). Approximately 30 mls of expanded culture was then spun down and pelleted at 3000×g, washed twice with Dulbecco's phosphate buffered saline (DPBS) and resuspended in 6 mls of DPBS. To improve the accuracy and reproducibility of bacterial challenge doses, we adapted the standard procedure for bacterial counting [Bubeck Wardenburg and Schneewind, supra]. Briefly, following resuspension of bacteria in 6 mls of DPBS, optical density at 600 nm (1.0 OD unit=approximately 600×$10^6$ bacteria) was used to determine preliminary bacterial concentrations and bacteria were then stored ON at 4° C. for use on the following day (Day 2). On the day of inoculation (Day 2), exact concentrations of bacterial inocula were computed from-analysis of plate counts from serial dilutions of *S. aureus* on TSB agar. A second series of bacterial plates were then set up to insure the viability of bacteria stored at 4 C, and these plates were assessed the day following bacterial challenge (Day 3). The viability of bacteria stored ON at 4° C. as determined from Day 3 TSB agar plates was equivalent to or 5-10% higher than the Day 2 counts.

Dermonecrosis Model

On the day of challenge, mice were anesthetized with isoflurane, hair was removed from the back and hind quarters with electric clippers (Oster, blade #50) and shaver (Remington MicroScreen) and mice were then injected intradermally with 0.05 mls of *S. aureus* at a typical concentration ranging from approximately 400-600×$10^6$/ml suspended in DPBS. Actual challenge doses were determined from bacterial plating and are indicated in the text or figure legends. Following inoculation, mice were followed for a period ranging from 2-6 days, at which time all mice were euthanized and lesions photographed. Chemical depilation was optionally performed as necessary to reveal the margins of lesions obscured by regrown or unshaven hair (VEET® Fast Acting Gel Cream Hair Remover, Reckitt Benckiser, Slough, UK). Lesion areas were determined by analyzing digital photographs using NIH Image J version 1.46r (Wayne Rasband, NIH) with calibration on a ruler included in each image. Lesion area data was subsequently analyzed using Prism (GraphPad Software, Inc., La Jolla Calif.). For mice challenged with the bioluminescent strain SAP149 only, in-life images of mice were obtained using a Xenogen Lumina II In vivo Imaging System (IVIS) (Caliper Life Sciences, Inc., Hopkinton Mass.) in the Veterinary Medicine Unit at the VA Ann Arbor Healthcare System. In-life imaging was performed at multiple time points according to themanufacturers protocols using Living Image 4.3.1 software (Caliper) for instrument control, data acquisition, and analysis. Luminescence was determined within a standard circular region of interest (ROI) fully covering and individually centered on the challenge site of each mouse. Dark Background Subtraction, Flat Field Correction, and Cosmic Correction were used, with a Binning of 8 and no smoothing. Measured ROIs were transferred to Microsoft Excel for formatting and subsequently to Prism for analysis. Images were captured with ROIs removed, with Color Scale Limits set to encompass the full range of intensities in all groups (25 to 6625) using a reverse rainbow Color Table, and with bioluminescence images superimposed on white light photograph of the mice. Enzyme-linked immunosorbent assay Antibody responses were assessed by ELISA essentially as described [Oscherwitz et al., *Infect. Immun.*, 77: 3380-3388 (2009)]. For analysis of antibodies specific for AT, wells of microtiter plates (Immulon 2, Thermo Labsystems, Franklin Mass.) were coated overnight at 4° C. with 100 ng of recombinant AT (Product #H9395, Sigma Biochemicals, St. Louis, Mo.) in a 0.05 M carbonate buffer pH 9.5. Bound antibody was detected with secondary biotinylated antibody specific for rabbit IgG (Southern Biotechnology, Birmingham, Ala.) followed by streptavidin-alkaline phosphatase and 4-nitrophenylphosphate (Roche, Indianapolis, Ind.).

Absorbance at 405 nm minus absorbance at 650 nm was determined using an ELISA reader (Emax microplate reader, Molecular Devices, Menlo Park, Calif.). Antibody titers were determined from serial two-fold dilutions of serum and represent the reciprocal dilution at the EC50 established using nonlinear regression to fit a variable slope sigmoidal equation to the serial dilution data using Prism 5.0 (GraphPad Software, Inc., San Diego, Calif.). Depending on assay setup, the lower limit of quantitation for the ELISA was 8 or 16. Commercial rabbit antisera against full length AT was employed as a positive control in the ELISA and TNA (Sigma, #S7531, Lot 042M4791, Sigma Biochemicals, St. Louis, Mo.) Each serum lot represents a pool comprised of sera from 2-3 hyperimmune rabbits.

Toxin Neutralization Assay

The ability of antibody to block AT cytotoxicity in vitro was assessed using the Jurkat T cell line (TIB-152, ATCC, Manassas, Va.). Briefly, Jurkat T cells were grown in culture in RPMI with 10% fetal bovine serum, penicillin-streptomycin and 50 μM 2ME (complete medium) in a humidified 6.5% $CO_2$ incubator. For each experiment, rabbit or mouse sera in duplicate was serially diluted with complete medium in polypropylene round-bottom 96 well plates in a final volume of 50 microliters per well. Recombinant AT reagent was prepared at four times (4×) the final concentration, with the final concentration (approximately 0.4 μg/ml) representing 3 to 4 multiples of the amount needed to kill 50% of the Jurkat T cells (Toxic dose 50% or $TD_{50}$). Each TNA assay was validated by performance of a contemporaneous AT titration. Serially diluted rabbit or mouse antiserum was added to the AT and the mixture was returned to the incubator for 30 minutes, after which time, 100,000 Jurkat T cells in 0.1 ml of complete medium were added to each well. Following a 2-hour incubation, 20 microliters of WST-8 reagent (Genscript USA Inc., Piscataway, N.J.) containing a water-soluble tetrazolium salt and electron mediator was added, and the absorbance at 450 nm minus absorbance at 650 nm was determined for each plate approximately 18 hours later using a Molecular Devices Emax microplate reader [Tominaga et al., Anal. Commun., 36: 47-50 (1999)]. Neutralization $ED_{50}$ (effective dilution at which 50% of cells are protected from cytotoxicity) titers were determined from serial two-fold dilutions of individual rabbit serum and represent the reciprocal dilution at the $EC_{50}$ established using nonlinear regression to fit a variable slope sigmoidal equation to the serial dilution data using Prism 5.0 [Hering et al., Biologicals, 32: 17-27 (2004)]. Depending on assay setup, the standard TNA assay has a lower limit of quantification of 4 or 8. Samples with TNA titers below the lower limit of quantification were assigned values of 4 or 8, respectively. For the analysis of peptide inhibition in the TNA, experimental serum samples were preincubated 1:1 with 32 μM of the 1-19 or 122-137 peptide for 1 hour at room temperature prior to analysis in the TNA.

Statistical Analysis

For determination of ELISA $EC_{50}$ and TNA $ED_{50}$ titers, four parameter logistic regression was used to fit variable slope sigmoidal equations to the serial dilution data. For lesion analysis, the Mann-Whitney U and Kruskal-Wallis test with Dunn's multiple comparison post test were used to assess significance between two or more than two groups, respectively. For analysis of rabbit antibody and TNA data, one way ANOVA with Newman Keuls multiple comparison post test was used for comparisons among more than two groups. For all statistical analysis, a p value of <0.05 was considered significant. All statistical analysis was performed using GraphPad Prism software version 5 (GraphPad Software, Inc., San Diego, Calif.).

Example 1

A Neutralizing Epitope Exists within the Pore-Forming Domain of AT

The structural and functional similarities of AT and PA led us to hypothesize that a neutralizing epitope exists in the pore-forming domain of AT. We therefore performed an initial experiment aimed at generating immunity in rabbits to amino acid 122-137 in AT. This region in AT demonstrates some structural and functional homology with the 2β2-2β3 loop of PA, but only 37% sequence identity when aligned (FIG. 1). We synthesized a MAP displaying the a.a sequence 122-137 from AT at the c-terminus of the T* helper T cell epitope from the circumsporozoite protein of Plasmodium falciparum which we have successfully employed previously for use in immunizing outbred rabbits [Oscherwitz et al., J. Immunol., 185: 3661-3668 (2010); Moreno et al., Int. Immunol., 3: 997-1003 (1991)]. Female NZW rabbits were then immunized 4 times at two-week intervals with the MAP and serum was collected two weeks after the fourth immunization for analysis.

Figure 2:
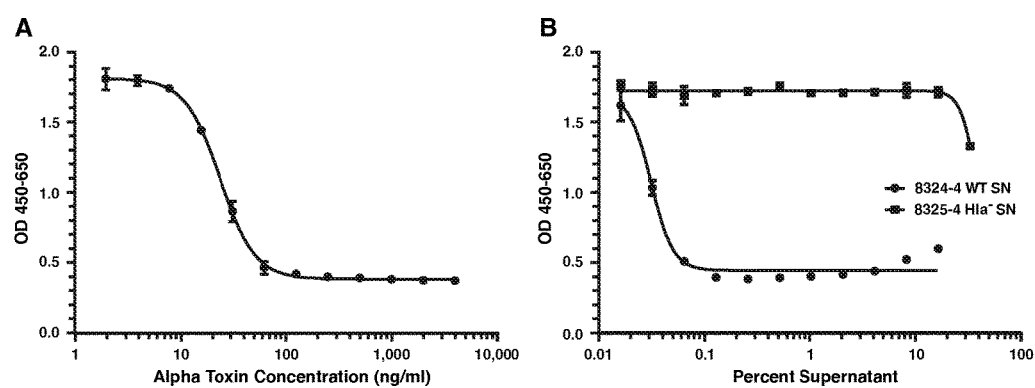
FIG. 2 shows Jurkat T cells are sensitive to recombinant and native AT in vitro. Shown are representative titrations demonstrating the cytotoxicity on Jurkat T cells in vitro of recombinant AT (A) and native AT (B) from the supernatants of overnight cultures of *S. aureus* 8325-4 (circles) or the isogenic (hla-) deletion mutant of 8325-4 (squares). Optical density (OD) increases with viability. The EC50 for recombinant AT=23.75 ng/ml and for native AT from the supernatant of the 8325-4 strain=0.03%. The supernatant from *S. aureus* 8325-4 (hla-) was not cytotoxic (B).

A robust in vitro neutralization assay was considered essential for functional evaluation and comparison of the antibody raised against the experimental constructs. While prevention of erythrocyte lysis has been employed to evaluate the neutralizing potential of antisera against AT in the S. aureus model, we wished to avoid the need for fresh RBCs for use in developing an optimized AT TNA, and further, desired an in vitro cell type which was likely a pathophysiologically-relevant immune cell target for AT in vivo. Both mouse and human T cells are highly sensitive to the effects of AT in vitro, and along with other leukocytes, are susceptible and likely pathophysiologically important cell targets for AT in vivo [Kennedy et al., J. Infect. Dis., 202: 1050-1058 (2010); Nygaard, PLoS One, 7: e36532 (2012); Molne et al., Clin. Exp. Immunol., 132: 209-215 (2003)]. We, therefore, developed an optimized toxin neutralization assay (TNA) which utilizes Jurkat, an immortalized human T cell line, which we found to be highly and reproducibly sensitive to recombinant AT, and to native AT from culture supernatants of MRSA (not shown) and MSSA strains (FIG. 2A, 2B).

Figure 3:
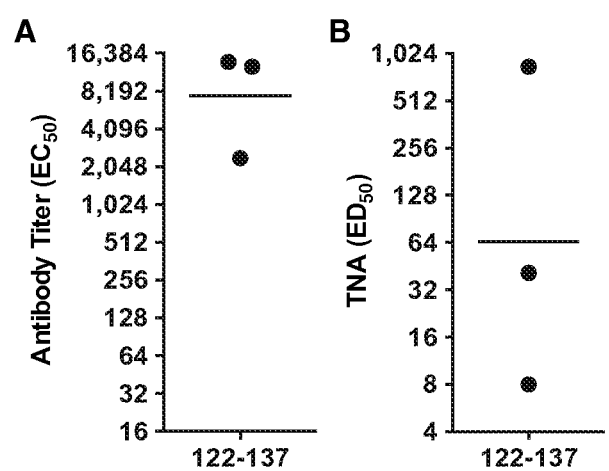
FIG. 3 shows that rabbit antibody against amino acids 122-137 from AT binds immobilized full-length AT by ELISA and protects Jurkat T cells in vitro. Three rabbits were immunized four times with a MAP displaying amino acids 122-137 from AT in an emulsion with CFA for priming immunizations and IFA for booster immunizations. Approximately 10 days after the final immunization, rabbit were bled and sera was evaluated by ELISA for reactivity with full length AT (A) and in the TNA (B).
Figure 4:
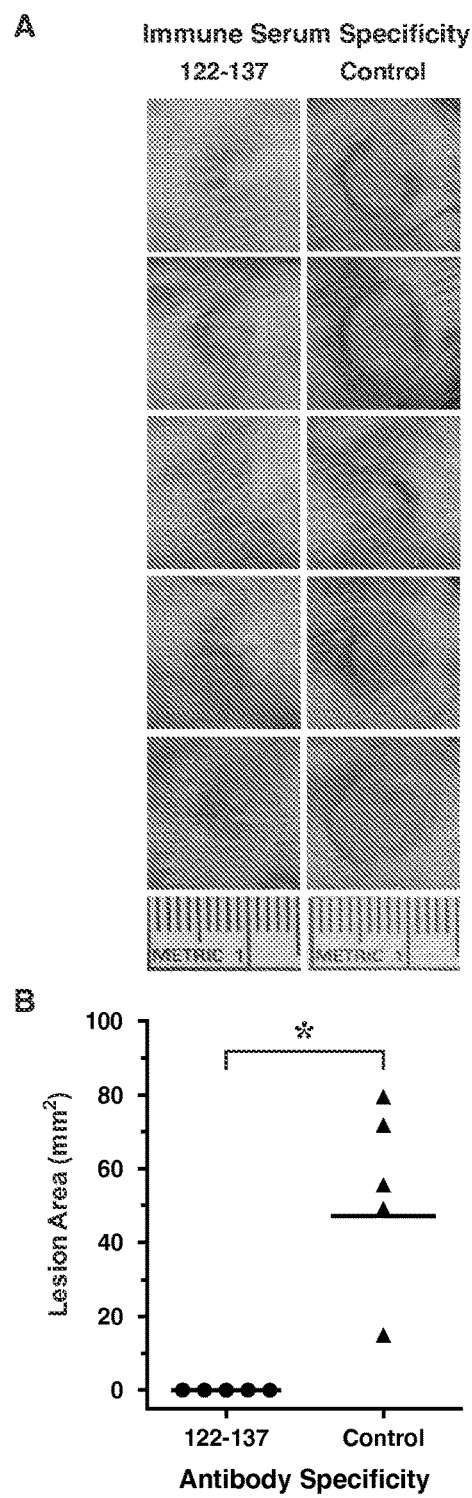
FIG. 4 shows that passive immunization of mice with AT-neutralizing rabbit antisera specific for AT amino acids 122-137 protects mice from intradermal challenge with *S. aureus* 8325-4. Five C57BL/6 mice/group were passive immunized with 0.5 mls of rabbit serum specific for amino acid 122-137 of AT, or irrelevant control rabbit serum. One day later, all mice were challenged i.d. with $20 \times 10^6$ CFUs of *S. aureus* 8325-4 and were followed for 48 hours. After 48 hours, all mice were euthanized and dermonecrotic lesion areas were photographed (A) and lesion areas were determined as described in Material and Methods and displayed graphically (B). Horizontal bars are geometric means. *p=0.0037, Mann-Whitney U test, one-tailed.
Figure 6:
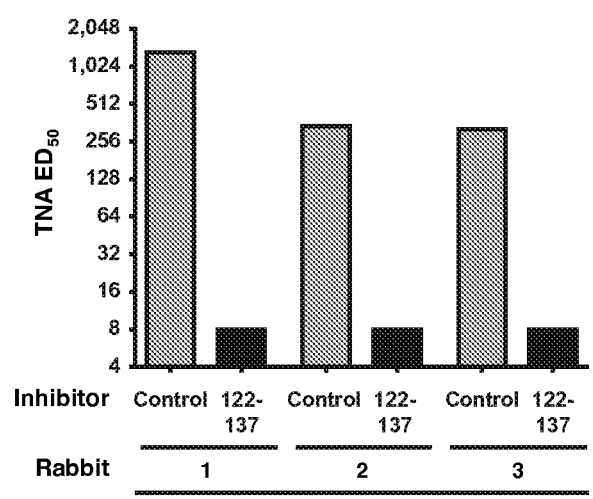
FIG. 6 shows that reincubation with the 122-137 peptide completely inhibits AT neutralization activity in the sera from rabbits immunized with MAP-119-139. Antiserum from each of 3 rabbits immunized four times with the MAP-119-139 shown in FIG. 5, was preincubated with 32 µM linear peptide, amino acid 122-137 or amino acid 1-19 (control) from AT for 1 hour at RT prior to assessment in the TNA.
Figure 7:
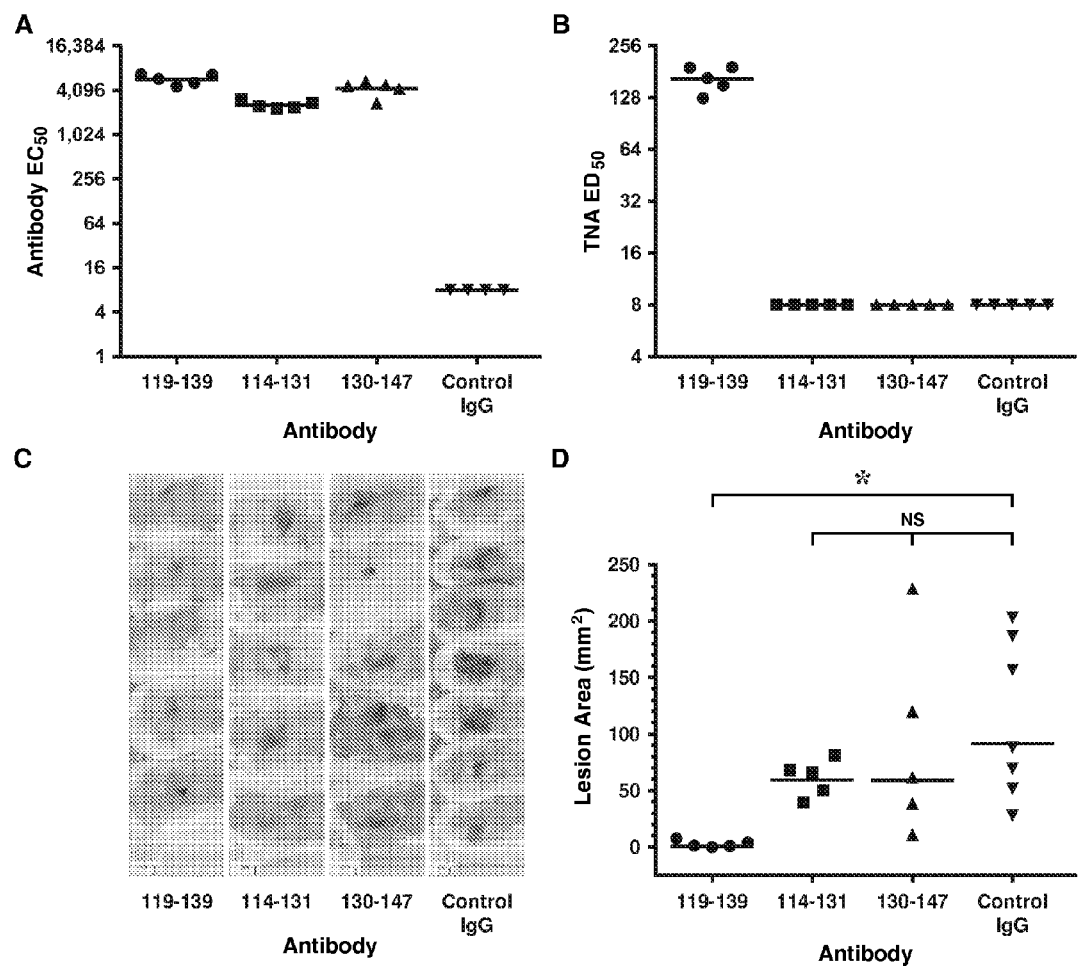
FIG. 7 shows that rabbit IgG specific for the 119-139 sequence from AT protects mice from LAC/USA300 mediated dermonecrosis. Groups of BALB/c mice (n=5) were passively immunized s.c. with normalized volumes of the respective affinity purified rabbit sera to establish approximately equivalent serum antibody titers in recipient mice. Approximately 48 hours later, all mice were bled and individual mouse sera were evaluated by ELISA for reactivity with immobilized AT (A) and in the TNA (B). All groups were then challenged i.d. with $38 \times 10^6$ LAC/USA300. Fourty-eight hours later, all mice were euthanized, lesions were photographed (C) and lesion areas determined (D). Mice passively immunized with rabbit IgG specific for the 119-139 sequence had significantly smaller lesions than mice receiving Control IgG (p=0.008, Kruskal Wallis, p<0.05 vs Control, Dunn's multiple comparison test). Lesion areas from groups of mice receiving the 114-131 and 130-147 IgG were not significantly different from the lesion areas of mice receiving the irrelevant control IgG. Horizontal lines in (A) and (B) represent geometric means.
Figure 8:
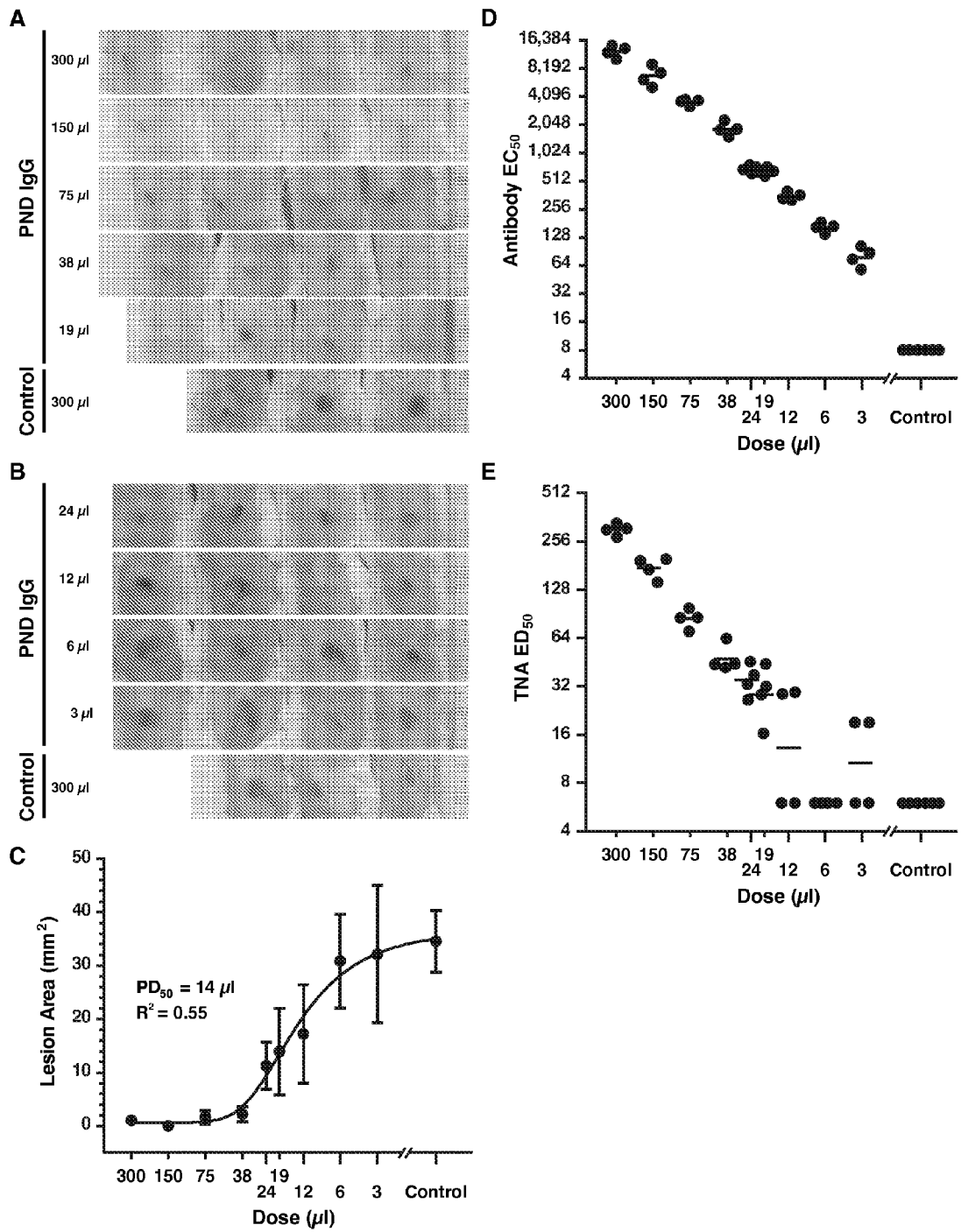
FIG. 8 shows dose response titration of PND Ab for protection of mice from LAC/USA300 dermonecrosis. Groups of BALB/c mice (n=4 except neg. controls, n=3) were passively immunized s.c. with two-fold dilutions of PND Ab starting with a dose of 300 µl (panel A) or 24 µl (Panel B). 48 hours later, mice were challenged i.d. with $32 \times 10^6$ (panel A) or $28 \times 10^6$ (panel B) CFUs LAC/USA300. Two days later, all mice were euthanized and photographed and lesion areas determined (C). Group-specific lesion areas were plotted against dose and four parameter non-linear regression was used to determine the $EC_{50}$ of 14 µl (R2=0.55) which represents the dose of PND Ab which prevented 50% of the maximal lesion area. Antibody and neutralization titers from the sera of mice passively immunized with PND-Ig were determined by ELISA (D) and in the TNA (E) from serum obtained from individual mice on the day of challenge. Data from (D) and (E) were then used to derive the Protective antibody 50% ($PA_{50}$) and Protective neutralization 50% ($PN_{50}$) which are the reciprocal serum antibody and neutralization titers required to reduce skin lesion dermonecrotic area by 50% of lesion formation (see, e.g., Example 3 and 4).

Sera from all three rabbits immunized with MAP 122-137 were found to be immunoreactive with immobilized AT by ELISA (FIG. 3A). When analyzed in the TNA, serum from one of the rabbits immunized with the MAP 122-137 demonstrated significant neutralization of AT in vitro (FIG. 3B). To evaluate whether this neutralizing activity would translate into mitigation of dermonecrosis following S. aureus infection, we passively immunized groups of C57BL/6 mice (n=5) i.p. with serum from the MAP 122-137-immunized rabbit which demonstrated neutralization, or with serum from a rabbit immunized with a T*-containing LND MAP immunogen (negative control) [Oscherwitz (2010), supra]. One day later, mice were challenged intradermally (i.d.) with $20 \times 10^6$ CFUs/mouse of S. aureus 8325-4, an MSSA strain which expresses high levels of AT [Munoz-Planillo et al., J. Immunol., 183: 3942-3948 (2009); Nilsson et al., Infect. Immun., 67: 1045-1049 (1999)]. Two days after bacterial challenge, mice were euthanized, photographed and lesion areas were determined. Mice passively immunized with the 122-137-specific rabbit antisera were completely protected from dermonecrosis, while mice passively immunized with the negative control antisera developed significant dermonecrosis (FIG. 4A, 4B, p=0.0037 Mann Whitney, FIG. 4A, 4B). The results confirmed that a neutralizing epitope, which we refer to as the pore neutralizing determinant (PND), is present in the β-pore forming domain of AT.

Example 2

In Vivo Mapping of the Pore Neutralizing Determinant in AT.

To more precisely map the PND of AT in vivo, we designed and synthesized MAPs for eliciting antibody against 3 additional overlapping sequences from AT, in addition to the 122-137 sequence (FIG. 5A). As in the first experiment, each MAP was synthesized collinearly with the T* helper T cell epitope, but in addition, all 4 MAPs were also separately synthesized collinearly with the P30 helper T cell epitope from tetanus toxin, which we have previously demonstrated to be an effective source of linked helper T cell stimulation in outbred rabbits [Oscherwitz et al., *Infect. Immun.*, 77: 5509-5518 (2009); Panina-Bordignon, supra]. Groups of rabbits, in turn, were immunized with a mixture of two MAPs, each containing the identical B cell target sequence from the β-pore domain of AT, but with separate, independent helper T cell epitopes, an approach we have previously determined increases antibody responses and decreases non-responsiveness in outbred rabbits. As shown in FIG. 5B, all 4 MAP constructs elicited high titer Ab reactive with AT by ELISA. When analyzed in the TNA, antisera from rabbits immunized with the 119-139 sequence demonstrated significantly higher levels of neutralization when compared to the antisera from rabbits immunized with the 122-137 sequence, or to antisera from rabbits immunized with MAPs displaying sequences n- and c-terminal to the 122-137 sequence, which had no detectable neutralization (FIG. 5C, p=0.022). The neutralizing antibody in the sera from all three rabbits immunized with the MAP 119-139 was, however, completely inhibitable in vitro through incubation with a 122-137 linear peptide (FIG. 6). Thus, though the 21-residue 119-139 segment may be more effective in eliciting the neutralizing antibodies (FIG. 5C), the critical residues defining the PND appear to fall within the nested 16-residue 122-137 segment, GNVTGDDTGKIGGLIG (SEQ ID NO: 14).

Example 3

PND-Specific Antibody Prevents *S. Aureus*-Induced Dermonecrosis In Vivo

To determine whether the results from the TNA would predict in vivo efficacy, we affinity purified antibody from the single rabbit with the highest antibody titer among each group of rabbits immunized with either the 119-139, 114-131 and 130-147 sequences, and then passively immunized groups of BALB/c mice (n=5) s.c. with the respective affinity purified antibodies. Two days later, mice were bled and then challenged i.d. with $38\times10^6$ LAC/USA300. We employed LAC/USA300 for these challenges since this MRSA strain is known to produce high levels of AT [Bubeck and Schneewind, supra], is highly virulent in the dermonecrosis model, and is the predominant strain implicated in CA-MRSA infections in the community [Kennedy, supra; Bubect Wardenburg and Schneewind, supra]. Analysis of mouse sera obtained on the day of challenge revealed that all groups of mice had approximately equivalent levels of serum antibody by ELISA, but as expected, only sera from mice in the 119-139 group demonstrated neutralization in the TNA (FIG. 7A,7B). Two days after challenge, all mice were sacrificed and lesions were photographed and analyzed. Mice passively immunized with 119-139 Ab were significantly protected from dermonecrotic lesions compared to mice passively treated with the Control-IgG (FIG. 7C, 7D, p=0.008). There was no statistical differences among lesion size in groups of mice passively immunized with the 114-131, 130-147 and Control-Ig.

Example 4

Antibody Specific for the PND of AT is Highly Potent for Preventing Dermonecrosis In a series of two experiments, we sought to determine the dose of affinity-purified 119-139 antibody (PND-Ig) required to prevent LAC/USA300-mediated dermonecrosis in mice. Additionally, we desired to establish, through analysis of mouse serum, the corresponding in vitro surrogates, namely antibody and neutralization titers, that might be used to quantitatively predict protection from dermonecrosis in this model. In the first experiment, groups of BALB/c mice (n=4) were passively immunized s.c. with serial two-fold dilutions of PND-Ig beginning at a dose of 300 μl per mouse. Two days later, mice were challenged intradermally with $32\times10^6$ CFUs of LAC/USA300. As shown in FIG. 8A, all doses between 300 μl to 38 μl almost completely prevented lesion formation compared to the negative control group. A follow-on titration was subsequently performed in identical fashion to the first titration to extend the titration to lower doses, beginning with a top dose of 24 μl (FIG. 8B). As in the first titration, mice were challenge 48 hours after passive immunization with LAC/USA300 and in this challenge received $28\times10^6$ CFUs. Two days after bacterial challenge, all mice were sacrificed and photographed (FIG. 8B). The procedures and actual challenge doses for the two experiments were nearly identical, and the treatment doses overlapped, enabling the results from the two titrations to be combined and analyzed collectively. Four parameter non-linear regression was used to derive the dose of PND-Ig required to prevent 50% of lesion size (Protective Dose 50% or $PD_{50}$) which was 14 μl (R2=0.55) in these experiments (FIG. 8C). To derive the in vitro correlates for protection from dermonecrosis, individual mouse sera obtained prior to challenge were analyzed by ELISA and in the TNA (FIG. 8D, 8E), and the data was then used, as in the $PD_{50}$ determinations, to derive the serum antibody and neutralization titers required to prevent 50% of lesion size in the dermonecrosis model (Protective Antibody 50%, $PA_{50}$, and Protective Neutralization 50%, $PN_{50}$, respectively) which expressed as reciprocal $EC_{50}$ and $ED_{50}$ titers, were 424 (R2=0.55) and 8.2 (R2=0.53), respectively.

Example 5

PND-Ig Enables Host Control of Bacterial Growth In Vivo

It has been established that the presence of functional AT is a requirement for *S. aureus*-mediated dermonecrosis in the mouse model, and that antibody-mediated neutralization of AT can mitigate the skin breakdown occurring as a consequence of intradermal challenge of mice with *S. aureus* [Tkaczyk et al. (2013), supra; Kennedy et al., supra; Foletti et al., supra; Tkczyk et al. (2012), supra]. Yet, while recombinant AT and native AT from culture supernatants of *S. aureus* have cytolytic effects on immune cell populations involved in innate and adaptive immune control of *S. aureus*, it is not clear to what extent neutralizing AT in vivo, in the context of intradermal challenge with *S. aureus*, contributes to control of bacterial proliferation as has been observed in some, but not all, systemic models of *S. aureus* infection [Cho et al., supra; Rauch et al., supra; Adhikari et al., supra; Nygaard et al., supra].

To examine the effect of neutralization of AT on bacterial burden over time, we employed passive immunization with PND-Ig, followed by challenge with SAP149, a luminescent and virulent derivative of the USA300 MRSA strain NRS384, which enabled in-life serial monitoring of bioluminescence as a validated surrogate for ex vivo CFU determination [Cho et al., supra; Prabhakara et al., supra; Plaut et al., supra; Miller et al., supra]. Prior to use of this strain for challenge, we determined that SAP149 produces high levels of AT, though approximately 25% lower than the amounts produced from LAC/USA300 evaluated in contemporaneous titrations of culture supernatants in the TNA (not shown). As a consequence, we administered challenge doses approximately 25% higher for SAP149 compared to prior experiments with LAC/USA300.

Figure 9:
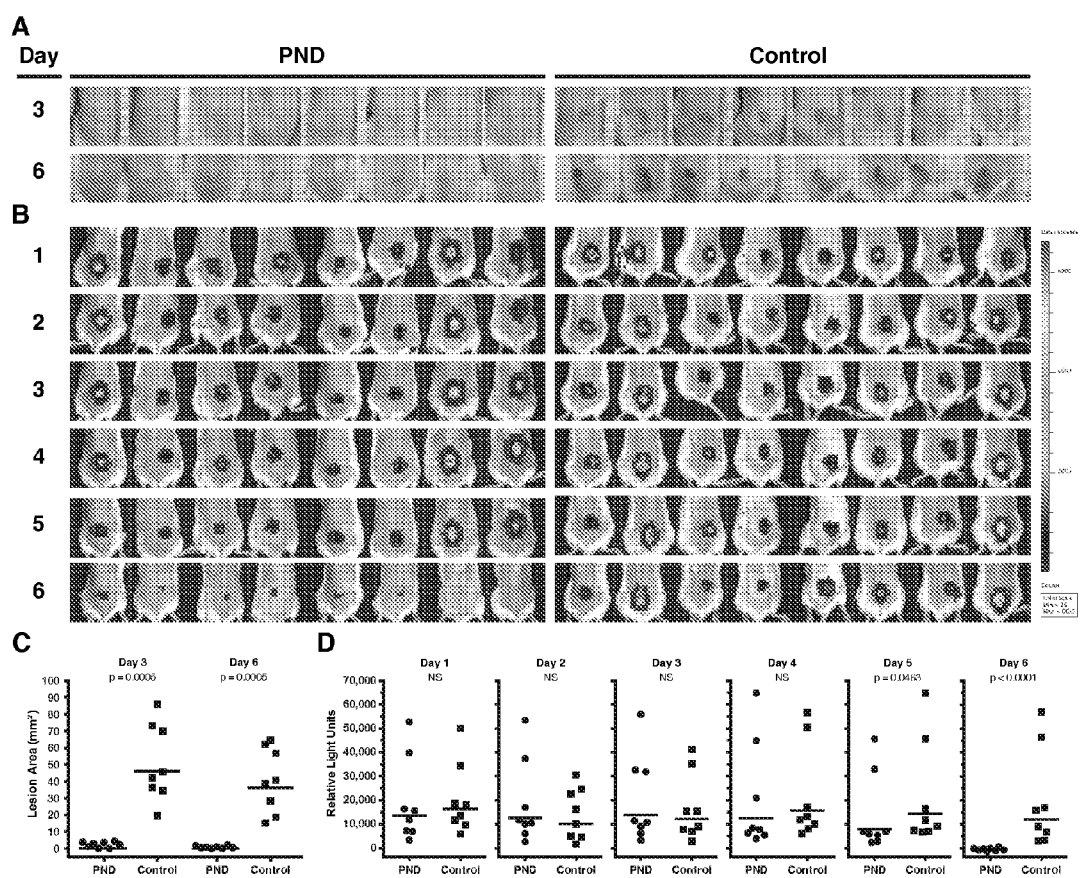
FIG. 9 shows that passive immunization with PND-Ig suppresses bacterial growth in vivo. Groups of mice (n=8) were passively immunized with 0.3 mls of PND-Ig or Control Ig 48 hours prior to i.d. challenge with $40 \times 10^6$ SAP149, a luminescent derivative of the USA300 stain NRS384 (47). (A) All mice were photographed at 3 and 6 days after challenge for determination of lesion size as described in Material and Methods. (C) PND-Ig mice were significantly protected from dermonecrosis compared to control-Ig mice at day 3 and day 6 (day 3: p=0.0005; day 6: p=0.0005, Mann-Whitney U, one-tailed). (B) All mice underwent daily in-life imaging for detection of bioluminescence as described in Material and Methods. (D) PND-Ig mice had significantly less luminescence and bacterial burden at days 5 and 6 after challenge compared to Control-Ig mice (day 5: p=0.046; day 6: p<0.0001, Mann-Whitney U, one-tailed).

Groups of BALB/c mice (n=8) were passively immunized s.c. with 0.3 mls of PND-Ig or control affinity purified Ab 48 hours prior to i.d. challenge of individual mice with $40 \times 10^6$ CFUs of SAP149. Mice were then serially imaged by IVIS for bioluminescence every 24 hours for 6 consecutive days. As expected, mice administered PND-Ig had significantly smaller lesions than mice treated with control-Ig when lesion areas were determined on days 3 and 6 (FIG. 9A, 9C, day 3: p=0.0005; day 6: p=0.0005). Despite the highly significant mitigation of dermonecrosis, however, the bacterial burdens of the PND-Ig and Control-Ig treated mice were not statistically different until days 5 and 6, whereupon the PND-Ig group demonstrated significant reductions in bacterial burden compared to the Control-Ig group of mice (FIG. 9B, 9D, day 5: p=0.046; day 6: p<0.0001). Indeed, on day 6, bioluminescence in the PND-Ig-treated mice had approached background levels, whereas day 6 bioluminescence in the Control-Ig treated mice was 97% of their Day 1 bioluminescence levels (FIG. 9D). The reductions in dermonecrotic lesion size and ultimately, in bacterial burden, were associated with serum geometric mean $ED_{50}$ reciprocal TNA titers of 246 and 96 in the PND-Ig mice on the day of challenge (Day 0) and on Day 6, respectively (not shown).

Example 6

Generation and Initial Testing of a Monoclonal Antibody Specific for the PND of AT The potency and effectiveness of PND-Ig suggested that a mAb with specificity for the PND could be a potentially effective preventative or therapeutic for *S. aureus* infections. We therefore screened mice which were immunized with the MAP 119-139 for the elicitation of neutralizing antibody against the PND. After splenic fusion and several rounds of screening, we isolated a monoclonal antibody (referred to as "3G6 mAb" herein) which was capable of binding immobilized AT by ELISA and neutralizing AT in vitro. The antibody was affinity purified from high cell density tissue culture flasks (Wheaton CELLine 1000) on protein A.

Figure 10:
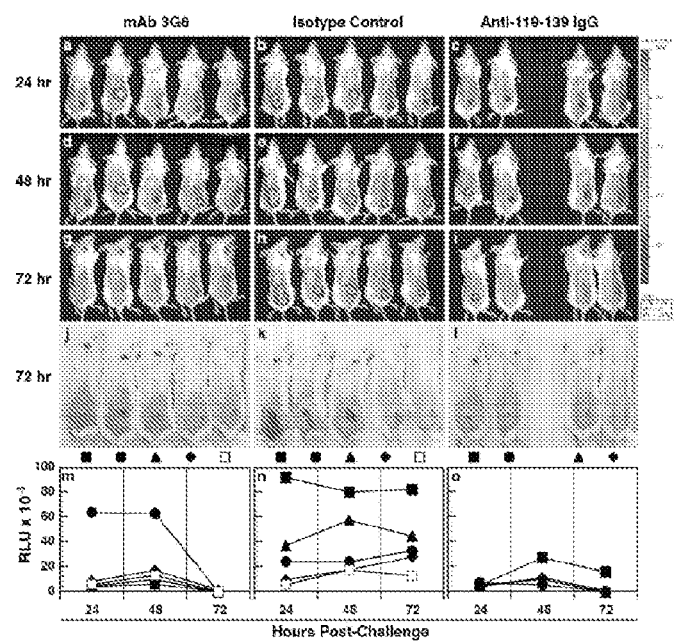
FIG. 10 shows a composite of bioluminescence (panel a-i), photographs (j-l) and graphs of RLU vs time for mice passively immunized with 3G6 mAb, isotype control or anti-119-139 mice (b,e,h) at all time points, and demonstrated significant reductions in lesion size compared to the isotype control at 72 hours (panels j,k, FIG. 7, and FIG. 8, p=0.028, one-way ANOVA).
Figure 11:
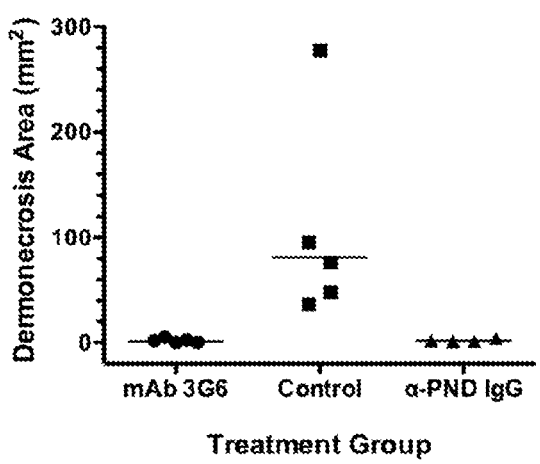
FIG. 11 shows dermonecrosis lesion area at 72 hours in mice passively immunized with 3G6 mAb.
Figure 12:
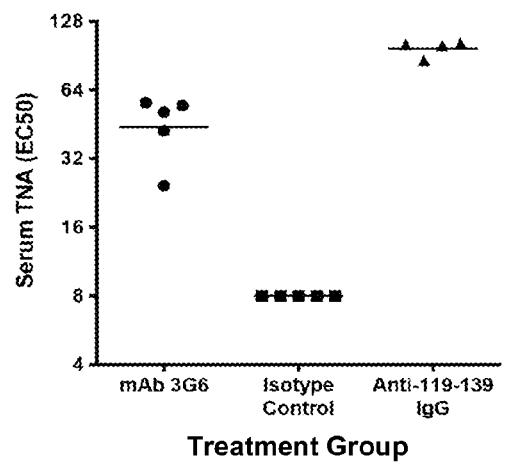
FIG. 12 shows TNA results from mice passively immunized with 3G6 mAb.

To assess whether mAb 3G6 had efficacy in vivo for prevention of dermonecrosis, we evaluated the mAb in the murine model of *S. aureus* induced dermonecrosis. Three groups of mice were injected s.c. with approximately 0.2 ug of 3G6 Ab or an isotype control Ab or 0.1 ml of the PND-IgG (positive control). Two days later, all mice were injected i.d. with $28E^6$ CFUs NRS384-lux (a gift of Dr. Scott Stibitz, FDA) which is a luminescent strain of USA300 previously validated for virulence (86). At 24, 48 and 72 hours after bacterial challenge, mice were imaged for bioluminescence by IVIS, and at 72 hours, all mice were euthanized and photographed and lesion areas were determined. As shown in FIG. 10, with the exception of a single mouse at 24 and 48 hours (panels a,d), mice receiving 3G6 had markedly reduced luminescence (CFUs) compared to the isotype control mice (b,e,h) at all time points, and demonstrated significant reductions in lesion size compared to the isotype control at 72 hours (panels j,k, FIG. 10, and FIG. 11, p=0.028, one-way ANOVA). Panels m,n,o show a graphical representation of the bioluminescence of mice from each group and highlight the evidence that neutralization of AT leads to marked reductions in bacterial burden. Of note also, there appears to be a strong correlation in the isotype control group between mouse RLUs (CFUs) at 72 hours (panel n) and eventual lesion size at euthanization (panel k) (Note: individual mice are aligned vertically throughout the panels), suggesting that the degree of bacterial growth, and likely the levels of AT, is related to the amount of tissue destruction. When mouse serum obtained prior to challenge was analyzed in the highly optimized and sensitive TNA, it was determined that the single mouse in the 3G6 group that demonstrated much higher RLUs at 24 and 48 hours (filled circles panel m) compared to the other 3G6 mice, was also the mouse with the lowest neutralization in the TNA (FIG. 12).

Example 7

3G6 mAb Prevents Dermonecrotic Lesions in Mice Challenged with Extremely High Doses of Methicillin-Resistant *S. Aureus* USA300 and Bacterial Proliferation in the Treated Mice Having demonstrated that 3G6 mAb can prevent dermonecrosis and decrease bacterial proliferation following intradermal challenge with *S. aureus* USA 300-lux, we set out to repeat these findings under more rigorous challenge conditions designed to better resolve the effects of the mAb to decrease bacterial proliferation. We, therefore, repeated the experiment but doubled the challenge dose to approximately $55E^6$ CFUs *S. aureus* USA 300-Lux and mice were followed out to 96 hours, an additional 24 hours compared to the first challenge. As in the first experiment, mice were passively immunized s.c. with 3G6 or an isotype control 48 hours prior to bacterial challenge.

Figure 13:
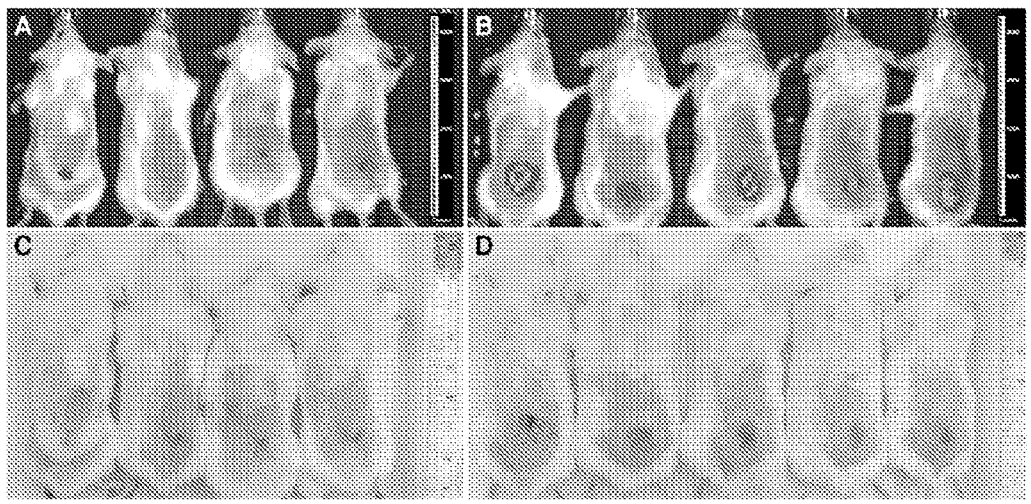
FIG. 13 shows a composite of bioluminescence (A,B) and photographs (C,D) at 96 hours post-challenge with *S. aureus* USA300-lux from groups of mice passively treated with PND-Ig (A,C) or isotype control Ab (B,D).
Figure 14:
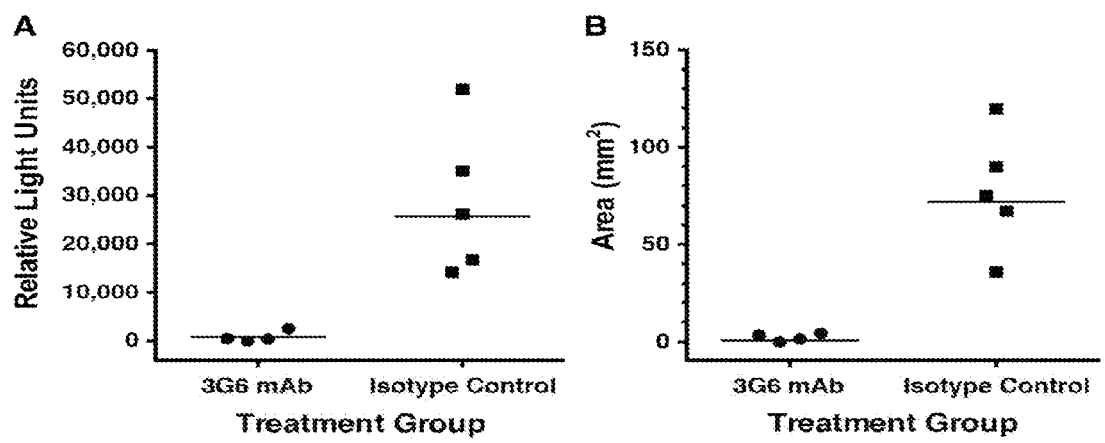
FIG. 14 shows graphical comparisons of bioluminescence (A) and lesion areas (B) at 96 hours from 3G6 and isotype control groups of mice.
Figure 15:
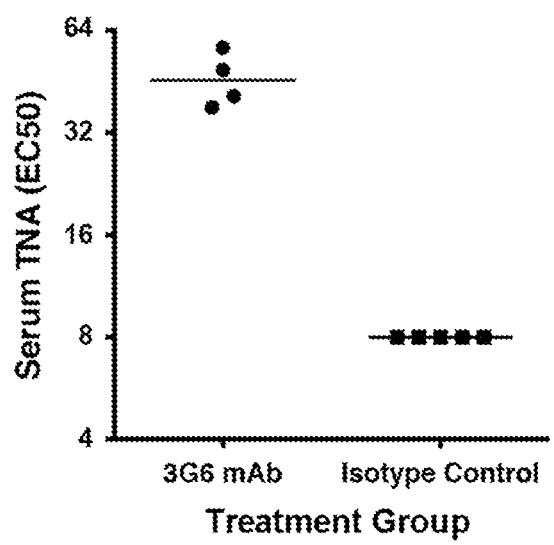
FIG. 15 shows AT toxin neutralization detectable in the sera of mice prior to intratracheal challenge with *S. aureus* USA300.

As shown in FIG. 13, mice administered 3G6 had markedly less luminescence apparent at 96 hours when assessed using bioluminescent imaging (panel A), reflecting the reduced bacterial proliferation in this group, compared to mice which received the isotype control Ab (panel B). These results were also consistent with the respective dermonecrotic lesion areas measured from mice at the 96-hour time point, which showed minimal to no lesions in the 3G6 group compared to the isotype control (FIG. 13, panels C and D). The differences in mean luminescence (bacterial proliferation) and lesion area in the respective groups at 96 hours were highly statistically significant (FIG. 14, panels A,B, p=0.009 and p=0.002, respectively, Two-tailed t test). As in the first dermonecrosis experiment, serum of mice from the 3G6 group, obtained prior to challenge, demonstrated the capacity to neutralize AT in vitro while serum from mice receiving the isotype control were devoid of such neutralizing activity (FIG. 15).

Overall, these results confirm and extend the results from the first dermonecrosis experiment to show that the 3G6 mAb is capable of preventing dermonecrotic lesions in mice challenged with extremely high doses of methicillin-resistant *S. aureus* USA300, and of decreasing and potentially preventing bacterial proliferation in the mAb-treated mice.

The results from the experiments evaluating the efficacy of the 3G6 mAb also serve to highlight the criticality of AT for enabling the epidermal breakdown which is characteristic of *S. aureus*-mediated dermonecrosis in the mouse model.

Example 8

The 3G6 mAb Protects Mice from the Lethal Intratracheal Administration of *S. Aureus* USA300-lux.

The demonstrated importance of AT as the critical virulence factor in the mouse pneumonia and peritonitis models suggests that these models, along with the sepsis model, may represent important, systemic models for evaluating PND-specific mAbs. We therefore, proceeded to evaluate the 3G6 mAb for efficacy in protecting mice from the lethal intratracheal administration of *S. aureus* USA300-lux in a model of primary pneumonia.

Figure 16:
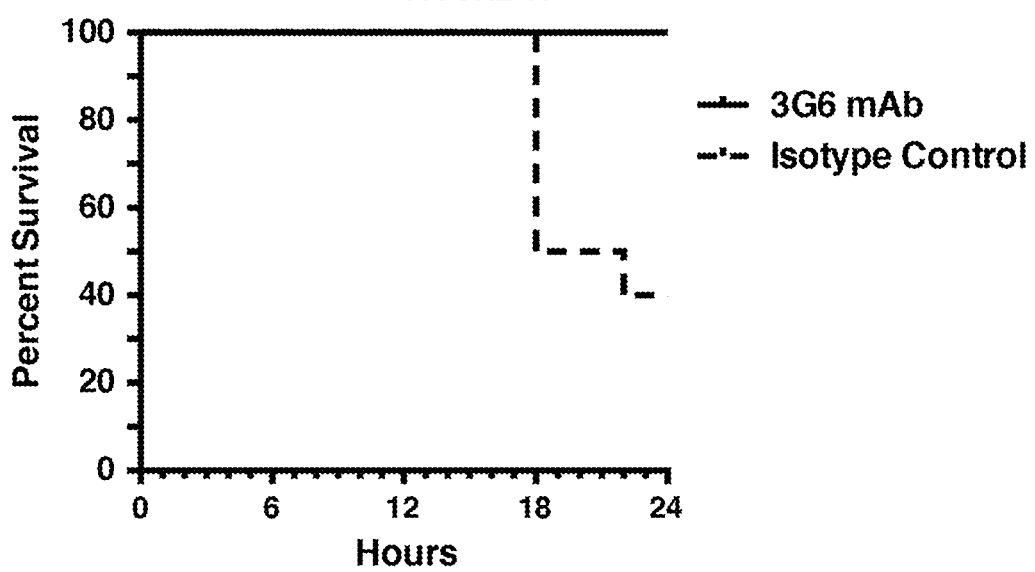
FIG. 16 shows Kaplan Meier survival curves for mice passively immunized with the 3G6 or isotype control Ab, and then challenged intratracheally with 90E6 *S. aureus* USA300-lux. 3G6-treated mice were significantly protected from death compared to the isotype control (p=0.004, Log-Rank test).

Following pilot studies to determine the $LD_{50}$ for mice challenged intratracheally with USA300-lux, we passively immunized groups of 8 week old C57BL/6 mice s.c. with approximately 200 μg of either the 3G6 mAb or the isotype control Ab. Three days later, all mice were challenged intratracheally with $90E^6$ CFUs of *S. aureus* USA300-lux and were followed for 24 hours, at which time all surviving mice were sacrificed for histological evaluation. As shown in FIG. 16, all mice (10/10) passively immunized with the 3G6 Ab were alive at 24 hours, while 60% of mice treated with the isotype control were dead (6/10, 3 LC, 3 no LC). The remaining control mice at the 24 hour time point looked ill, manifested as hunched posture, raised fur and general lethargy, but had not yet technically met our predetermined humane endpoint criteria and were therefore considered survivors. All mice which had received the 3G6 mAb were active and did not appear ill. Histological evaluation by an objective veterinary pathologist of representative lung sections from 3G6-treated mice revealed normal lung architecture and little evidence of inflammation in the 3G6 treated mice, whereas sections from the control-treated mice demonstrated multifocal acute necrotizing peri-bronchiolitis with predominately neutrophils many of which were necrotic, and loss of normal alveolar architecture.

Figure 17:
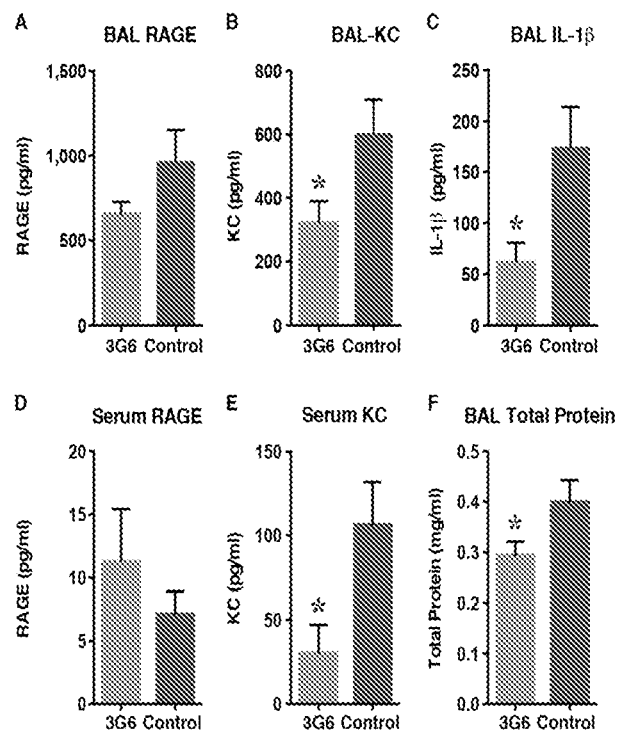
FIG. 17 shows BAL and serum analysis from 3G6-treated and isotype-treated mice four hours after intratracheal challenge with MRSA.

A second experiment was designed to evaluate whether 3G6 mAb could prevent lung permeability injury and inflammation at a very early time point post-challenge. For these studies, two groups of C57BL/6 mice (n=9 for 3G6 mAb, n=10 for isotype control Ab) were pre-treated i.p. with 200 μg of either mAb 3G6 or the control mAb. Twenty four hours later, all mice were challenged intratracheally with $184 \times 10^6$ CFUs of *S. aureus* USA300. Four hours after challenge, all mice were euthanized, and bronchoalveolar lavage (BAL) fluid and serum were analyzed for assessment of permeability injury (proteins) and specific inflammatory mediators (FIG. 17, panels A-F, *p<0.05). Mice treated with the 3G6 Ab demonstrated a significant reduction in BAL proteins even at this very early time point (panel F). BAL levels of the neutrophilic CXC chemokine, KC and levels of IL1-β, an early marker of inflammation in *S. aureus* pneumonia, were also significantly lower in the BAL of 3G6 mAb-treated mice compared to the isotype control (IL1-β was undetectable in the sera of both 3G6 and isotype control groups, not shown). RAGE, the receptor for advanced glycation endproducts, and a cleavage-product of ADAM10, was lower in the BAL from the 3G6 mice compared to the isotype control group, though the differences had not yet reached statistical significance (Panel A, p=0.08) at this early time point. A representative H&E stained section from a 3G6-treated mouse demonstrated normal appearing lung at low and high power. In contrast, low and high power images from a representative lung section obtained from an isotype control-treated mouse showed acute imflammatory changes as evidenced by lung alveolar septa which are expanded by marginating neutrophils with early emigration into alveoli.

Example 9

Humanization of mAb 3G6

3G6 will be humanized using the guided selection approach retaining the heavy chain CDR3 (HCDR3) which employs a stepwise exchange of the mouse for human variable regions using phage display technology. The CDR3 regions on the heavy and light chains are the most important determinants of antibody specificity and affinity and retention of an original CDR3 enables preservation of the original specificity with minimal residual mouse sequence.

Once the optimal construct is derived using guided selection, we will build out the full-length heavy and light chain genes with human IgG1 sequence and transfer these into separate expression plasmids. These will be transfected into HEK293 cells for transient expression to obtain 1-2 mg of HmAb which will be sent to the Oscherwitz lab for characterization. HEK-derived HmAb will be tested by ELISA to evaluate binding and in the TNA to assure acceptable specific activity (AT neutralization normalized for mass of Ab) compared to the 3G6 mAb, and the affinity will be determined by BIAcore surface plasmon resonance analysis through ProteinX Labs. These metrics will enable precise bench-marking of the HmAb to assure that its performance meets and/or exceeds that of the original 3G6 mAb.

Development of a cell line that stably expresses the HmAb will be performed using a CHO-K-1 cell line adapted for suspension culture employing a bicistronic vector enabling balanced expression of heavy and light chains. A clonal cell line will be derived from high expressing cells and a research cell bank (RCB) will be prepared. Cells from the RCB will be expanded at pilot scale to produce milligrams of HmAb for subsequent studies. Ultimately, the RCB will provide the basis for developing a cGMP Master Cell Bank. The cells will be derived and maintained in the absence of antibiotic selection by the use of a vector expressing glutamine synthase (GS), and growth and expression will be in chemically defined, animal component free (CDACF) media which will be employed in all culturing of these cells. The HmAb produced from RCB-derived cells will be purified to homogeneity by protein A and ion exchange chromatography.

Example 10

In vitro measurement of the ability of antibody to neutralization a toxin that mediate pathology in vivo offers a reliable method for modeling efficacy of such antibody for preventing or mitigating toxin-related diseases like anthrax and *S. aureus* infection. In both models, in vitro toxin neutralization has been shown to correlate with and predict the in vivo efficacy of such antisera or mAbs to prevent or treat disease [Little et al., *Vaccine*, 22: 422-430 (2004); Hering et al., *Biologicals*, 32: 17-27 (2004); Adhikari et al., *PLoS One*, 7: e38567 (2012); Migone et al., *N. Eng. J. Med.*, 361: 135-144 (2009)]. Differences in the in vitro neutralization activities of different antisera or mAbs may be attributable, in part, to the different and potentially unique mechanisms of action by which antibodies to distinct epitopes act to neutralize the target molecules. For example, mAbs have been described for use in anthrax that inhibit binding of protective antigen to the anthrax toxin cellular receptor, and some of these mAbs have been shown to prevent inhalation anthrax in animal models [Migone et al., supra; Little et al., *Infect. Immun.*, 56: 1807-1813 (1998)]. In the *S. aureus* model, antisera raised to a vaccine targeting the N-terminus of AT, where a distinct neutralizing epitope has now been described [Oscherwitz et al., *Mol. Immunol.*, 60: 62-71 (2014)], has been shown to neutralize AT in vitro, and the levels of in vitro neutralization serve as a correlate of protective immunity in vivo in models of *S. aureus* pneumonia, sepsis, and dermonecrosis [Adhikari et al., supra; Tkaczyk et al., *Clin. Vaccine. Immunol.*, 29: 377-385 (2012)]. The in vitro neutralizing activity of the N-terminal-specific antisera, therefore, can be considered a good predictor of the efficacy of the sera when passively administered as a preventative or therapeutic in in vivo models of *S. aureus* disease.

Figure 18:
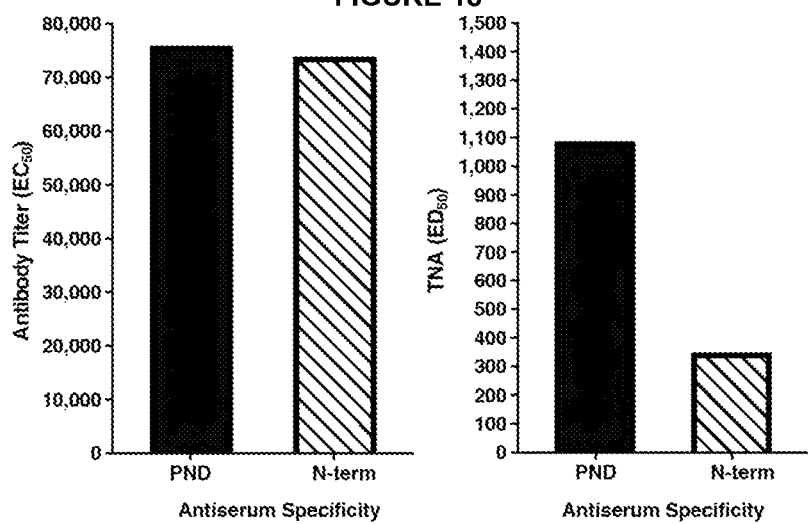
FIG. 18 shows the antibody (panel A) and toxin neutralization (B) titers of affinity purified rabbit antiserum raised to either N-terminal- or PND-focused immunogen from AT. As shown, the antisera have been normalized to have similar antibody titers but the PND-specific antisera has 3-fold higher neutralization activity compared to the N-terminal-specific antisera.

Antisera raised to PND-containing immunogens or the PND-specific mAb 3G6 described herein have in vitro toxin neutralizing activity contemplated to be distinct from the neutralizing activity of other antisera and mAbs specific for different neutralizing epitopes within the AT molecule. A comparison of the in vitro neutralization activity between commercially available rabbit antisera to the N-terminal AT epitope [Little et al. (2014), supra] and rabbit antisera to the PND is informative. When both antisera are normalized to have identical antibody titers to AT, the PND-specific antisera is shown to be three times more potent than the N-terminal specific antisera for neutralizing the cytotoxic effects of AT on the Jurkat human T cell line (FIG. 18). Specific activity can be understood as a metric reflecting the amount of functional Ab (neutralizing activity) relative to the amount of overall Ab [Oscherwitz et al., *Infect. Immun.*, 77: 5509-5518 (2009)]. In these terms, the PND antisera have a higher specific activity. The differences in specific activity between the N-terminal-specific antisera and the PND-specific antisera would be expected to parallel differences in in vivo potency in animal models of *S. aureus* disease.

It is contemplated that the potency of antibody against the PND relates to the nature of the PND in pore formation.

CONCLUSION

Our data demonstrates that the PND linear neutralizing epitope is present in the β-pore region of AT, and comprises residues 122-137. Rabbit antibody elicited to a MAP displaying amino acid 119-139 from AT was capable of neutralization in vitro, and the antibody-mediated neutralization was completely inhibitable with a linear peptide comprising amino acids 122-137. The linear nature of this neutralizing epitope, as opposed to a conformational epitope comprised of non-contiguous sequences, is contemplated by the invention to be useful for incorporation as part of a mono- or multivalent vaccine for MRSA. The studies described in the examples show that mAb against the PND is highly effective at protecting mice from tissue damage and bacterial proliferation in a rigorous dermonecrosis model, and further, demonstrate that the mAb can protect mice from a highly lethal pulmonary challenge with a clinically relevant methicillin-resistant strain of *S. aureus*. Moreover, serum neutralization levels determined through use of the TNA, appear to be a reliable in vitro correlate and surrogate for protection in the dermonecrosis model.

While the present invention has been described in terms of specific embodiments, it is understood that variations and modifications will occur to those skilled in the art. Accordingly, only such limitations as appear in the claims should be placed on the invention.

All documents referred to in this application are hereby incorporated by reference in their entirety with particular attention to the content for which they are referred.

We claim:

1. An immunogenic composition comprising an immunogen consisting essentially of the *S. aureus* alpha toxin epitope GNVTGDDTGKIGGLIG (SEQ ID NO: 14) or an immunogenic equivalent thereof, wherein the immunogenic equivalent is a peptide consisting essentially of an amino acid sequence at least 90% identical to (SEQ ID NO: 14).

2. The immunogenic composition of claim 1 comprising an immunogen consisting of the *S. aureus* alpha toxin epitope GNVTGDDTGKIGGLIG (SEQ ID NO: 14) or an immunogenic equivalent thereof, wherein the immunogenic equivalent is a peptide consisting essentially of an amino acid sequence at least 90% identical to (SEQ ID NO: 14).

3. The immunogenic composition of claim 1 comprising an adjuvant.

4. The immunogenic composition of claim 1 comprising one or more additional *S. aureus* immunogens.

5. A method of inducing an immune response to *S. aureus* alpha toxin in a subject comprising administering an immunogenic composition to the subject in an amount effective to induce protective immunity against *S. aureus* infection, wherein the immunogenic composition comprises an immunogen consisting essentially of the *S. aureus* alpha toxin epitope GNVTGDDTGKIGGLIG (SEQ ID NO: 14) or an immunogenic equivalent thereof, and wherein the immunogenic equivalent is a peptide consisting essentially of an amino acid sequence at least 90% identical to (SEQ ID NO: 14).

6. A method of treating *S. aureus* infection in a subject comprising administering an immunogenic composition to the subject, wherein the immunogenic composition comprises an immunogen consisting essentially of the *S. aureus* alpha toxin epitope GNVTGDDTGKIGGLIG (SEQ ID NO: 14) or an immunogenic equivalent thereof, and wherein the immunogenic equivalent is a peptide consisting essentially of an amino acid sequence at least 90% identical to SEQ ID NO: 14.

7. The method of claim 6 further comprising administering one or more antibiotics.

8. The method of claim 7 wherein the antibiotic is tetracycline, doxycycline, minocycline, trimethoprim-sulfamethoxazole, rifampin, clindamycin, vancomycin, linezolid, daptomycin, tigecycline, telavancin, dalbavancin, oritavancin, ceftobiprole, mupirocin or iclaprim.

9. The method of claim 6 further comprising administering one or more additional antibody products, wherein the additional antibody product or products are specific for an *S. aureus* epitope different from the alpha toxin epitope GNVTGDDTGKIGGLIG (SEQ ID NO: 14).

10. The method of claim 9 wherein the *S. aureus* epitope of claim 9 is not an alpha toxin epitope.

* * * * *

UNITED STATES PATENT AND TRADEMARK OFFICE
CERTIFICATE OF CORRECTION

PATENT NO. : 10,080,790 B2
APPLICATION NO. : 15/511827
DATED : September 25, 2018
INVENTOR(S) : Jon Oscherwitz et al.

Page 1 of 1

It is certified that error appears in the above-identified patent and that said Letters Patent is hereby corrected as shown below:

In the Claims

In Column 42, Line 37, the word "doxicycline," should be -- doxycycline, --

Signed and Sealed this
Twenty-fifth Day of June, 2019

Andrei Iancu
*Director of the United States Patent and Trademark Office*

SEQUENCE LISTING

```
<160> NUMBER OF SEQ ID NOS: 14

<210> SEQ ID NO 1
<211> LENGTH: 21
<212> TYPE: PRT
<213> ORGANISM: Staphylococcus aureus

<400> SEQUENCE: 1

Gly Phe Asn Gly Asn Val Thr Gly Asp Asp Thr Gly Lys Ile Gly Gly
1               5                   10                  15

Leu Ile Gly Ala Asn
            20

<210> SEQ ID NO 2
<211> LENGTH: 10
<212> TYPE: PRT
<213> ORGANISM: Mus musculus

<400> SEQUENCE: 2

Thr Phe Ser Arg Thr Thr Tyr Gly Val His
1               5                   10

<210> SEQ ID NO 3
<211> LENGTH: 16
```

```
<212> TYPE: PRT
<213> ORGANISM: Mus musculus

<400> SEQUENCE: 3

Ala Met Trp Lys Asp Gly Thr Thr Asp Tyr Asn Ala Ala Phe Met Ser
1               5                   10                  15

<210> SEQ ID NO 4
<211> LENGTH: 7
<212> TYPE: PRT
<213> ORGANISM: Mus musculus

<400> SEQUENCE: 4

Arg His Tyr Thr Val Asp Phe
1               5

<210> SEQ ID NO 5
<211> LENGTH: 16
<212> TYPE: PRT
<213> ORGANISM: Mus musculus

<400> SEQUENCE: 5

Arg Ser Ser Gln Thr Ile Val His Arg Asn Gly Asn Ile Tyr Leu Glu
1               5                   10                  15

<210> SEQ ID NO 6
<211> LENGTH: 7
<212> TYPE: PRT
<213> ORGANISM: Mus musculus

<400> SEQUENCE: 6

Lys Val Ser Ser Arg Phe Ser
1               5

<210> SEQ ID NO 7
<211> LENGTH: 9
<212> TYPE: PRT
<213> ORGANISM: Mus musculus

<400> SEQUENCE: 7

Phe Gln Gly Ser Arg Ile Pro Phe Thr
1               5

<210> SEQ ID NO 8
<211> LENGTH: 111
<212> TYPE: PRT
<213> ORGANISM: Mus musculus

<400> SEQUENCE: 8

Leu Glu Gln Ser Gly Pro Val Leu Val Gln Pro Leu Gln Ser Leu Ala
1               5                   10                  15

Ile Thr Cys Ser Val Ser Thr Phe Ser Arg Thr Thr Tyr Gly Val His
                20                  25                  30

Trp Ile Arg Gln Ser Pro Gly Lys Gly Leu Glu Trp Leu Gly Ala Met
            35                  40                  45

Trp Lys Asp Gly Thr Thr Asp Tyr Asn Ala Ala Phe Met Ser Arg Leu
        50                  55                  60

Ser Ile Thr Gln Asp Asn Ser Lys Ser Gln Val Phe Leu Glu Ile Asn
65                  70                  75                  80

Asp Leu Gln Ser Asp Asp Thr Gly Thr Tyr Phe Cys Phe Asp Arg His
                85                  90                  95

Tyr Thr Val Asp Phe Trp Gly Gln Gly Thr Ser Val Thr Val Ser
```

<210> SEQ ID NO 9
<211> LENGTH: 110
<212> TYPE: PRT
<213> ORGANISM: Mus musculus

<400> SEQUENCE: 9

```
Val Leu Thr Gln Thr Pro Leu Ser Leu Ser Val Ser Leu Gly Asp Gln
1               5                   10                  15

Ala Ser Ile Ser Cys Arg Ser Ser Gln Thr Ile Val His Arg Asn Gly
            20                  25                  30

Asn Ile Tyr Leu Glu Trp Tyr Leu Gln Lys Pro Asp Gln Ser Pro Lys
        35                  40                  45

Leu Leu Ile Tyr Lys Val Ser Ser Arg Phe Ser Gly Val Pro Asp Arg
    50                  55                  60

Phe Ser Gly Ser Gly Ser Gly Thr Asp Phe Thr Leu Arg Ile Ser Arg
65                  70                  75                  80

Val Glu Ala Glu Asp Leu Gly Ile Tyr Tyr Cys Phe Gln Gly Ser Arg
                85                  90                  95

Ile Pro Phe Thr Phe Gly Gly Gly Thr Lys Leu Glu Ile Lys
            100                 105                 110
```

<210> SEQ ID NO 10
<211> LENGTH: 63
<212> TYPE: DNA
<213> ORGANISM: Staphylococcus aureus

<400> SEQUENCE: 10

```
ggattcaacg gtaatgttac tggtgatgat acaggaaaaa ttggcggcct tattggtgca      60
aat                                                                    63
```

<210> SEQ ID NO 11
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 11

```
Glu Tyr Leu Asn Lys Ile Gln Asn Ser Leu Ser Thr Glu Trp Ser Pro
1               5                   10                  15

Cys Ser Val Thr
            20
```

<210> SEQ ID NO 12
<211> LENGTH: 21
<212> TYPE: PRT
<213> ORGANISM: Artificial sequence
<220> FEATURE:
<223> OTHER INFORMATION: Synthetic polypeptide

<400> SEQUENCE: 12

```
Phe Asn Asn Phe Thr Val Ser Phe Trp Leu Arg Val Pro Lys Val Ser
1               5                   10                  15

Ala Ser His Leu Glu
            20
```

<210> SEQ ID NO 13
<211> LENGTH: 26
<212> TYPE: PRT

```
<213> ORGANISM: Artificial sequence
<220> FEATURE:
<223> OTHER INFORMATION: Synthetic polypeptide

<400> SEQUENCE: 13

Gln Ser Val Glu Ile Asn Cys Thr Arg Pro Asn Asn Asn Thr Arg Lys
1               5                   10                  15

Ser Ile His Met Gly Pro Gly Arg Ala Phe
            20                  25

<210> SEQ ID NO 14
<211> LENGTH: 16
<212> TYPE: PRT
<213> ORGANISM: Staphylococcus aureus

<400> SEQUENCE: 14

Gly Asn Val Thr Gly Asp Asp Thr Gly Lys Ile Gly Gly Leu Ile Gly
1               5                   10                  15
```